US009186651B2

(12) United States Patent
da Silva Pinto et al.

(10) Patent No.: US 9,186,651 B2
(45) Date of Patent: Nov. 17, 2015

(54) METAL ORGANIC FRAMEWORK MODIFIED MATERIALS, METHODS OF MAKING AND METHODS OF USING SAME

(75) Inventors: Marcia da Silva Pinto, Burgfelderstrasse (CH); Cesar Augusto Sierra Avilla, Bogota (CO); Juan Paulo Hinestroza, Ithaca, NY (US)

(73) Assignee: Cornell University, Ithaca, NY (US)

(*) Notice: Subject to any disclaimer, the term of this patent is extended or adjusted under 35 U.S.C. 154(b) by 221 days.

(21) Appl. No.: 13/818,798

(22) PCT Filed: Aug. 25, 2011

(86) PCT No.: PCT/US2011/049083
§ 371 (c)(1), (2), (4) Date: Jun. 25, 2013

(87) PCT Pub. No.: WO2012/027538
PCT Pub. Date: Mar. 1, 2012

(65) Prior Publication Data
US 2013/0274087 A1 Oct. 17, 2013

Related U.S. Application Data

(60) Provisional application No. 61/376,956, filed on Aug. 25, 2010.

(51) Int. Cl.
*B01J 20/22* (2006.01)
*B01D 53/04* (2006.01)
(Continued)

(52) U.S. Cl.
CPC ............... *B01J 20/226* (2013.01); *B01D 15/00* (2013.01); *B01D 53/02* (2013.01); *B01D 53/0407* (2013.01); *B01J 20/28023* (2013.01); *B01J 20/28033* (2013.01); *B01J 20/321* (2013.01);
(Continued)

(58) Field of Classification Search
CPC .... B01D 53/02; B01D 53/04; B01D 53/0407; B01D 2253/204; B01D 2257/108; B01D 2257/406; B01D 2257/502; B01D 2257/504; B01D 2257/7025; B01J 20/226; B01J 20/28023; B01J 20/28033; B01J 20/3204; B01J 20/321; B01J 20/3212; B01J 20/3217; B01J 20/3265; Y02C 10/08; Y02C 20/20; C07F 1/005
USPC .............. 96/154; 95/116, 128, 139, 140, 143; 210/660
See application file for complete search history.

(56) References Cited

U.S. PATENT DOCUMENTS

| | | | |
|---|---|---|---|
| 7,637,983 | B1 | 12/2009 | Liu et al. |
| 2004/0019143 | A1 | 1/2004 | Koloski et al. |

(Continued)

OTHER PUBLICATIONS

Zhang et al., Gas permeability properties of Matrimid membranes containing the metal-organic framework Gu-BPY-HFS, Journal of Membrane Science, vol. 313, pp. 170-181. Jan. 16, 2008.
(Continued)

*Primary Examiner* — Frank Lawrence
(74) *Attorney, Agent, or Firm* — Hodgson Russ LLP

(57) ABSTRACT

MOF (metal organic framework)-modified materials and methods of making and methods of using same. The MOFs are covalently bound to the materials. Examples of suitable materials include fibers and thin films. The MOF-modified materials can be made by forming MOFs in situ such that they are covalently bound to the materials. The MOF-modified materials can be used in methods where gases and/or toxic chemicals are absorbed.

12 Claims, 28 Drawing Sheets

$Cu_3(C_9H_3O_6)_2$

(51) Int. Cl.

| | |
|---|---|
| ***B01D 53/02*** | (2006.01) |
| ***C07F 1/00*** | (2006.01) |
| ***B01J 20/28*** | (2006.01) |
| ***B01J 20/32*** | (2006.01) |
| ***B01D 15/00*** | (2006.01) |

(52) U.S. Cl.

CPC .......... *B01J 20/3204* (2013.01); *B01J 20/3212* (2013.01); *B01J 20/3217* (2013.01); *B01J 20/3265* (2013.01); *C07F 1/005* (2013.01); *B01D 2253/204* (2013.01); *B01D 2257/108* (2013.01); *B01D 2257/406* (2013.01); *B01D 2257/502* (2013.01); *B01D 2257/504* (2013.01); *B01D 2257/7025* (2013.01); *Y02C 10/08* (2013.01); *Y02C 20/20* (2013.01)

(56) References Cited

U.S. PATENT DOCUMENTS

| | | | | |
|---|---|---|---|---|
| 2008/0296527 | A1 | 12/2008 | Liu et al. | |
| 2009/0169857 | A1 * | 7/2009 | Fischer et al. ............. | 428/304.4 |
| 2010/0043636 | A1 * | 2/2010 | Hwang et al. .................. | 95/127 |

OTHER PUBLICATIONS

Venna et al., Highly Permeable Zelite Imidazolate Framework-8 Membranes for Co2/CH4 Separation, J. A.M. Chem. Soc., vol. 132, pp. 76-78. Dec. 16, 2009.

* cited by examiner $Cu_3(C_9H_3O_6)_2$

METAL ORGANIC FRAMEWORK MODIFIED MATERIALS, METHODS OF MAKING AND METHODS OF USING SAME

CROSS-REFERENCE TO RELATED APPLICATIONS

This application claims priority to U.S. provisional patent application No. 61/376,956, filed Aug. 25, 2010, the disclosure of which is incorporated herein by reference.

STATEMENT REGARDING FEDERALLY SPONSORED RESEARCH

This invention was made with government support under contract no. OSP 5390 awarded by the Defense Threat Reduction Agency (DTRA). The government has certain rights in the invention.

FIELD OF THE INVENTION

The present disclosure generally relates to materials to which metal-organic frameworks are covalently attached. The present disclosure further relates to a method of making materials to which metal-organic frameworks are covalently attached.

BACKGROUND OF THE INVENTION

Metal-Organic Frameworks (MOFs) and Metal-Organic Polyhedra (MOPs) are a recently-identified class of porous polymeric material composed of highly selective assemblies exhibiting large surface areas and composed of metals linked through organic groups. MOFs are focus of research for a range of applications such as "host" molecules for gases and other molecules. In addition, due to their high porosity MOFs allow the "host" molecules to be captured inside their structure. The trapped molecule can then be part of a selective chemical reaction.

Despite the newness of this field, gas sorption properties of MOFs suggest many practical applications. For example, the application of MOFs-polymer mixed matrix membranes such as polyimides has been demonstrated. The MOFs allowed the polymer to infiltrate the pores of these structures, improving the interface and mechanical properties of the polymer. Also of recent interest has been the utilization of MOF films on stainless steel fibers for solid-phase microextraction of volatile and harmful benzene homologues. MOFs selectively adsorbed methane; therefore mixed matrix membranes from MOFs and poly (3-acetoxyethylthiophene) (PAET). The results showed that when compared to the pure polymer, the mixed matrix membranes exhibited enhanced methane permeability.

BRIEF SUMMARY OF THE INVENTION

In an aspect, the present invention provides MOF-modified materials. In an embodiment, the present invention provides a material having at least one dimension of from 10 nm to 1000 μm, and at least one MOF covalently bound to the material. For example, the MOF is covalently bound to the fiber through a functional group selected from alkyl, ester, acetate, alcohol, amine, amide, carboxylate, and thiol. In another embodiment, the present invention provides compositions comprising MOF-modified materials.

For example, the material is an organic fiber or an inorganic fiber or a thin film or an organic or inorganic material. For example, the fiber is cellulose, ester-modified cellulose fibers or anionic-modified cellulose fibers. For example, the MOF is MOF 199, MOF 76, or a mixtures thereof.

In an example, the material (e.g., fibers or thin films) have from 0.1 to 45% by weight MOFs. In another example, the fibers have at least 1% surface coverage of MOFs.

In another aspect, the present invention provides a method for selectively absorbing a gas or liquid. In an embodiment, a MOF-modified material of the present invention is exposed to a mixture comprising at least one gas or liquid, where the material selectively absorbs the at least one gas or liquid. For example, the gas is hydrogen or methane, ammonia, carbon monoxide, or carbon dioxide.

In another aspect, the present invention provides methods of making the MOF-modified materials. In an embodiment, the present invention provides a method of making MOF-modified materials, comprising the steps of: providing a material having at least one dimension of from 10 nm to 1000 μm; and exposing the material to a mixture of MOF precursors, under conditions resulting in the formation of at least one MOF that is covalently bound to the material, thereby forming MOF-modified materials where the MOFs are covalently bound to the material. For example, the material can be in the form of fibers or thin film. In an example, the fibers are modified cellulose fibers, such as ester-modified cellulose fibers or anionic-modified cellulose fibers.

For example, wherein the MOF-modified material is formed by exposing modified cellulose fibers to a mixture comprising 1,3,5-benzenetricarboxylic acid, copper (II) acetate ($Cu(OAc)_2$), and triethylamine.

DETAILED DESCRIPTION OF THE INVENTION

Figure 1A:
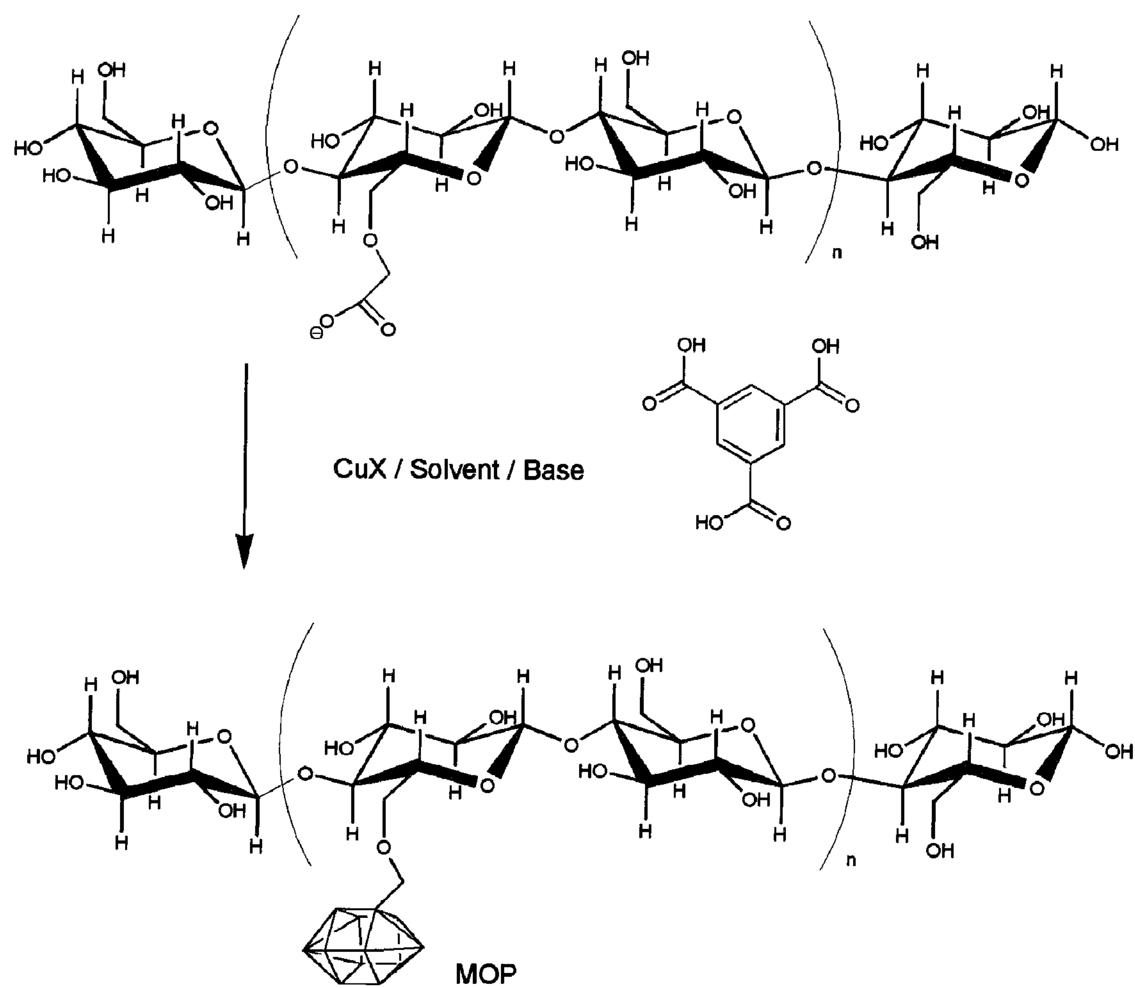
FIG. 1. Example of in situ formation of metal-organic framework ((A) an example of a MOP; and (B) an example of a MOF) chemically bonded to anionic-modified cellulose fibers. Where X represents the counterion for the copper salt.

The present invention provides MOF-modified materials. The present invention also provides methods for making such MOF-modified materials. The MOFs are covalently attached to the fibers. Without intending to be bound by any particular theory, it is considered that the covalent attachment of MOFs has the advantage of extending the half-life of the attached compound or allowing their continued use in devices. The term "MOF-modified materials" is meant to describe materials having at least one MOF covalently bound to it.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

In an aspect, the present invention provides MOF-modified materials and compositions comprising MOF-modified materials. In an embodiment, the material has at least one dimension from 10 nm to 1000 μm and at least one metal-organic framework (MOF) covalently bound to the material. In an embodiment, the material is a fiber. In another embodiment, the material is a thin film. The MOF is covalently bound to the material through a functional group. Examples of suitable functional groups include alkyl groups, ester groups, acetate groups, alcohol groups, amine groups, amide groups, carboxylic acid groups and thiols. In an embodiment, substantially all of the MOFs are covalently bound to the material. By substantially, it is meant, in various examples, that at least 80, 90, 95, 99, 99.9 and 99.99% of the MOFs are covalently bound to the material. In an embodiment, all of the MOFs in the composition are covalently bound to the material. In another embodiment, there are no free MOFs in the composition.

In an embodiment, the present invention provides a composition comprising an anionic-modified cellulose fiber and at least one MOF is covalently bound to the anionic-modified fiber. The modified fibers and films can be derived from, for example, cellulose, zirconia, and polyamide (e.g., Nylon™) materials.

The materials can be inorganic materials or organic materials. The materials have at least one dimension of from 10 nm to 1000 μm, including all values to the nm and ranges therebetween. For example, the material can be a fiber having at least one such dimension or a thin film having at least one such dimension.

It is desirable that the materials have surface functional groups for MOF binding or for in situ formation of MOFs or be able to undergo chemical surface modification to provide such functional groups. The materials can be naturally occurring or synthetic (i.e., manmade). Suitable materials are commercially available. Suitable organic materials include cellulose wool, rayon, fique, curaua and coconut materials, polyolefins, polyamides (e.g., Nylon™ materials) and other polymers such as polyacrilamide and polyacrylonitrile (PAN), and polyimides. Suitable inorganic materials include zirconia fibers. Any of these materials can be, for example, in the form a fiber or a thin film.

The fibers can be of any size. Examples of suitable sizes include 50 nm to 1000 nm, including all values to the nm and ranges therebetween. For example, cellulose fibers from 50 μm to 80 μm in diameter can be used.

The thin films can be of any area that can be deposited. For example, a suitable thickness of the thin film is 40 nm to 5 mm, including all values to the nm and ranges therebetween.

In an embodiment, the fibers are cellulose fibers. Cellulose is the most abundant natural polymer in nature and is an important source of raw material for "green" products. Cellulose based fibers are used for coatings, laminates, optical films, pharmaceuticals, foods and textiles. When describing cellulose based fibers, a population of fibers typically at least about 50 μm in diameter, in another aspect from 50 to about 80 μm in diameter are used in the anionic-modified cellulose fibers and films. Conversion of cellulose hydroxyl groups to, for example, esters lead to various useful forms such as fibers and solutions for coating films or membranes. Thus, the use of anionic-modified cellulose and carboxylated cellulose allow a great range of applications of these materials.

In an embodiment, when the material is cellulose fibers the fibers can be surface modified. For example, such modification, e.g., by standard organic chemistry reactions, includes the substitution of at least one hydroxyl groups present on the cellulose surface by other groups containing single and multiple carbon-nitrogen, carbon-sulfur and/or carbon-oxygen bonds. This new surface functional group of the cellulose can have a cyclic or acyclic aliphatic structure with the capacity of making one, two or more electrostatic interactions with the metal core of the growing MOP, then acting as a mono or polyvalent chelant specie.

In an embodiment, the fibers are organic fibers coated with an inorganic material. For example, the fibers can be PAN fibers coated with zirconium oxide.

Any MOF can covalently bonded to the materials. MOFs are crystalline nanoporous materials built of small metal-containing clusters connected three-dimensionally by polyfunctional organic ligands. MOFs also include, for example, metal organic polyhedra (MOPs), zeolite imidazolate frameworks (ZIFs), and covalent organic frameworks (COFs).

Examples of suitable polyfunctional organic ligands include aliphatic and aromatic tricarboxylates. Other examples of suitable organic ligands include ethanedioic acid, propandioic acid, butandioic acid, pentandioic acid, 1,2-benzendicarboxylic acid, 1,3-benzendicarboxylic acid, 1,4-benzendicarboxylic, 2-hydroxy-1,2,3-propanetricarboxylic acid, 3,4-dihydroxy-3-cyclobutene-1,2-dione and 1,2,3-triazole, and pyrrodiazole (or salts thereof) and substituted analogues thereof. Examples of suitable MOFs include those having di or trivalent metal clusters including Cu, Zn, Mn, and Tb.

In an example, the MOFs comprise copper (e.g., HKUST-1 (or MOF 199) is a copper benzene-tricarboxylate porous material, turquoise-blue crystals). Metal-organic framework 199" ("MOF-199") is desirable as it is readily synthesized and has open metal sites, which can provide high storage capacities of hydrogen and methane. It is a framework comprised of dimeric cupric tetracarboxylate ($Cu_2(CO_2)_4$) cluster units with short Cu—Cu internuclear separation linked by trimesate. It can be represented by the chemical formula $Cu_2(C_9H_3O_6)_{4/3}$.

In another example, the MOF comprise terbium (e.g., MOF-76). "Metal-organic framework 76" ("MOF-76") is a framework comprised of a Tb—O—C units are comprised of 7-coordinated Tb(III) (terbium III) centers. Six carboxylates and a terminal $H_2O$ unit bind each Tb atom. The channels between the tetragonal arrangement of the terbium and carboxylates are filled with molecules of DMF. It can be represented by the chemical formula $Tb(C_9H_3O_6)(H_2O)_{3/2}(DMF)$.

In another example, the MOFs are formed from 1,3,5-benzenetricarboxylic acid ligands. In this example, the MOFs comprise 1,3,5-benzenetricarboxylate groups. Examples of suitable MOFs include MOF 199 and MOF 76.

In an embodiment, the MOF-modified fibers have the same MOFs. The fibers can be modified with mixtures of MOFs. In an embodiment, the MOF-modified fibers have at least two different MOFs. In another embodiment, the MOF-modified fibers have at least 10 different MOFs.

The fibers have at least one MOF covalently attached to the fiber. The extent of MOF modification of the fibers can, for example, be described in terms of weight % (wt %) loading of the MOF-modified fibers or MOF surface coverage of the fibers. In an embodiment, the fibers have from 0.1 to 45 wt %, including all values to 0.1 wt % and ranges therebetween, loading of MOFs. In another embodiment, the MOF surface coverage of the MOF-modified fibers is from 0.1% to 95%, including all values to the tenth of a percentage and ranges therebetween.

In an embodiment, the present invention provides a composition comprising a MOF-modified material of the present invention or a mixture of such materials. In another embodiment, the present invention provides a composition consisting essentially of the MOF-modified materials or a mixture of such materials. In yet another embodiment, the present invention provides a composition consisting of the MOF-modified materials or a mixture of such materials.

In another aspect, the present invention provides methods for making MOF-modified materials fibers. For example, the MOFs can be formed in situ in the presence of the materials. In any of the methods described herein the material or modified material can be a fiber, a modified fiber, thin film or modified thin film.

Figure 1B:
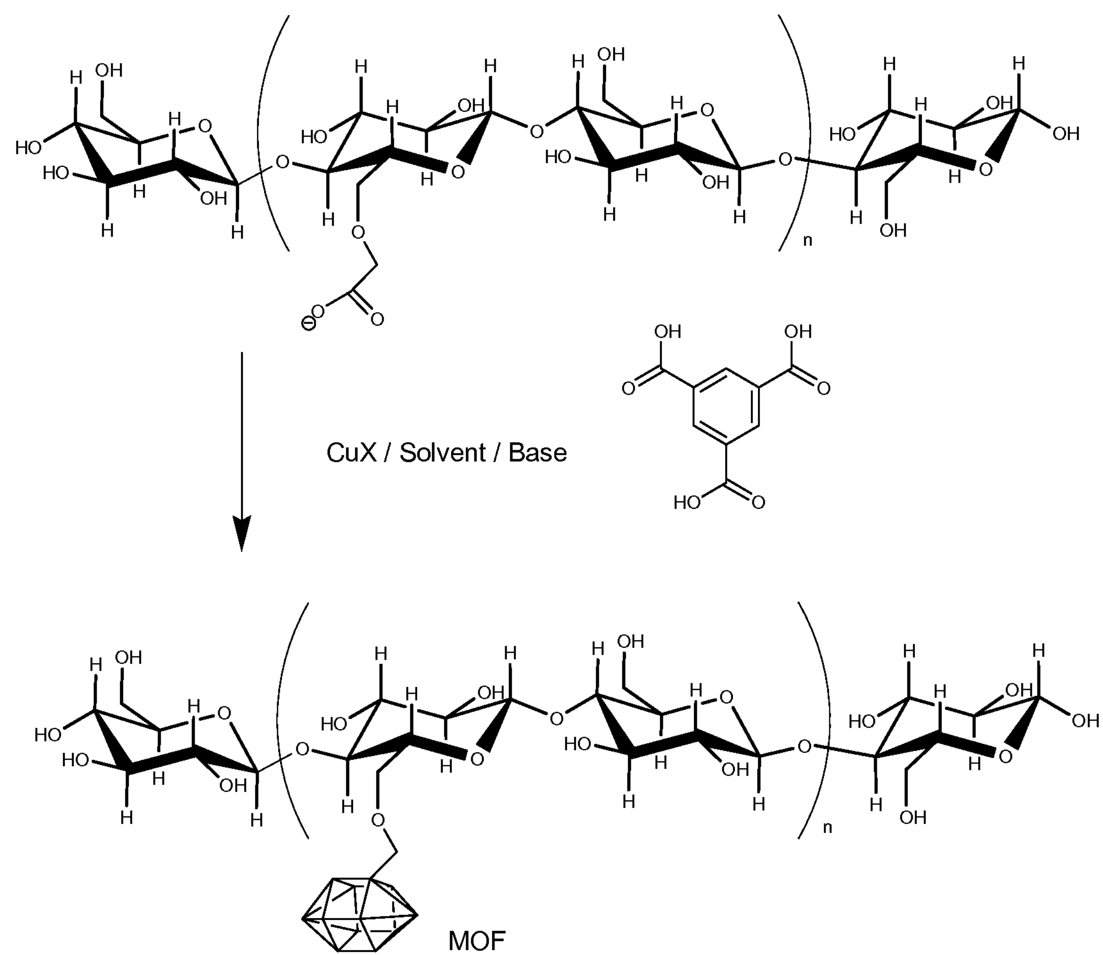

In an embodiment, a method of making MOF-modified fibers comprises the steps of: providing a suitable material; exposing the material to MOFs, under conditions such that MOF-modified materials are formed. For example, FIG. 1 shows a methodology for attachment of MOF 199 to anionic-modified cellulose fibers.

In another embodiment, a method of making MOF-modified materials comprises the steps of: providing a suitable material; exposing the material to a mixture of MOF precursors, under conditions such that MOF-modified materials are formed. In this embodiment, the MOFs are formed in situ in the presence of the materials such that the MOFs are covalently bound to the fibers.

In the methods of the present invention, it is considered that determination of suitable reaction conditions (e.g., reagent amounts, solvent(s), reaction temperature, reaction atmosphere is within the purview of one having skill in the art).

In an embodiment, the MOP-modified materials are isolated from the reaction mixture from any of the methods.

The materials are disclosed herein. The materials can be, for example, fibers or thin films.

The fibers are described herein. In the methods, the fibers can be used in an unmodified form or a modified form. The fibers can be modified to comprise functional groups. The fibers can be modified in such a way that any MOF can be assembled on the fibers due to the flexibility of the MOF architecture. For example, the fibers can be modified with ester groups or anionic groups. For example, the modified cellulose fibers can be ester-modified cellulose fibers or anionic-modified cellulose fibers.

Prior to the chemical attachment of MOFs to cellulose-based fibers the surface of these fibers may be modified by a chemical modification. For example, modification of a hydroxyl (—OH) group(s) can be modified to a carboxylate group(s) (—COO) to yield the anionic-modified cellulose. Due to the advantage of an abundance of hydroxyl groups on the surface of cellulose, different chemical modifications can be made to introduce stable negative or positive electrostatic charges. Such chemical modification of the fibers aims at improving the chemical attachment between the polymeric matrix of the fibers and MOFs.

The modified fibers can be anionic modified cellulose. Anionic-modified cellulose is cellulose that has been chemically modified so that there is a functional group (e.g., a tethered component that possesses a carboxylate anion on the cellulose fiber) providing a means for attachment of a MOF.

The modified fibers can be anionic-modified zirconia. For example, modified zirconia is zirconia that has been modified first by reacting it water and tetrachlorosilane to obtain a metal organic framework of oxygen, silicon, and zirconium. Subsequently, the Si—OH bonds are chemically modified so that there is a functional group (e.g., a tethered component that possesses carboxylate anion) on the zirconia fiber providing a means for attachment of a MOF.

In the methods, the thin films can used as deposited. In the methods, the thin films can also be modified as described for the fibers above.

Any MOF can be formed such that it is covalently attached to the fiber. In an embodiment the MOF is MOF 199, MOF 76, or a mixture thereof. In another embodiment, MOF 199, MOF 76 is formed in situ in the presence of a fiber such the MOF is covalently attached to the fiber.

Mixtures of MOF precursors are known in the art. For example, the mixture of MOF precursors comprises a metal precursor, a ligand, a catalyst (e.g., a base) and a solvent (or mixture of solvents). The metal precursor can be a M(II) or M(III) salt or complex, where M is a metal. Any organic base can be used. An example of a suitable organic base is triethylamine.

A wide variety of solvents can be used. Examples of suitable solvents include ethanol, methanol, and DMF. An example of a mixture of solvents is (X:Y:Z), where X is chosen from DMF, Y is chosen from a group consisting of ethanol (EtOH) and methanol (MeOH), and Z is chosen from water ($H_2O$). In an example, the mixture is a 1:1:1 by volume mixture of DMF:EtOH:$H_2O$.

The notation "M(II)" and "M(III)" denote metals in a +2 and +3 oxidation state respectively. M can be chosen from the alkaline earth metals, such as Be, Mg, Ca and Sr, the lanthanides, such as Ce, Sm, Eu, Ho, Tb, and Er, transition metals, such as Ti, Zr, Ni, Co, Cr, Cu, Zn, Ag, Cd, Pd, Ir, Au, and Hg, post-transition metals, such as Al, Ga, In, Sn, and Pb, and metalloids, such as Ge, As, Sb, and Te. In various embodiments, M is Cu, Zn, and Tb.

The term "ligand" is meant to describe a molecule or functional group that binds to a central metal atom to form a coordination complex. The nature of this metal-ligand bond can range from ionic to covalent. These ligands are typically mono-, di-, and trivalent ligands. For example, the ligands used to form the MOF can be 1,3,5-benzenetricarboxylic acid (derivatives thereof and salts thereof). Examples of suitable polyfunctional organic ligands include aliphatic and aromatic tricarboxylates. Other examples of suitable organic ligands include that can be used to construct MOFs include ethanedioic acid, propandioic acid, butandioic acid, pentandioic acid, 1,2-benzendicarboxylic acid, 1,3-benzendicarboxylic acid, 1,4-benzendicarboxylic, 2-hydroxy-1,2,3-propanetricarboxylic acid, 3,4-dihydroxy-3-cyclobutene-1,2-dione and 1,2,3-triazole, and pyrrodiazole (or salts thereof) and substituted analogues thereof.

In an example, the MOF-modified fibers are made by exposing modified cellulose fibers to a mixture comprising 1,3,5-benzenetricarboxylic acid, copper (II) acetate, and triethylamine.

In another aspect, the present invention provides uses of the MOF-modified materials. In an embodiment, the present invention provides a method for selectively absorbing a gas or liquid (e.g., toxic gases or toxic liquids) comprising exposing the MOF-modified materials of the present invention to a mixture comprising at least one gas or liquid, wherein the material selectively absorbs the at least one gas or liquid. In various examples, at least 80, 90, 95, 99, 99.9% of the at least one gas or liquid is selectively absorbed as determined by methods known in the art. In various examples, the gas can be hydrogen, methane, ammonia or carbon monoxide. For example, MOF-modified materials where the MOF comprises zinc or copper can be used to selectively adsorb methane. In various examples, the liquids include can be organic and inorganic solvents, gasoline, oil, and the like. For example, the method can be used to treat liquid waste.

Conditions (e.g. exposure time, temperature, etc.) for the method can be varied to achieve the desired result. In an example, the method can be carried out at temperatures up to 100° C.

Other methods include cleaning of air streams. Examples of such methods include filtration of exhaust effluent (e.g., effluent from chimneys) and purification systems.

Due to the fascinating structure of the MOFs and great potential applications in various fields, these structures were selected as components for attachment to, for example, cellulosic fibers. Although there are thousands of different types of MOFs, in the present invention MOF 199 was chosen due to the easiness of its synthesis and the presence of open metal sites, one of the most important attributes in high storage capacities of hydrogen and methane. Furthermore, it is reported that the addition of particles to polymeric matrix represents an important method for enhancing the performance of these polymeric materials for gas separations. Thus, one of the applications of MOFs attached to fibers would be the utilization in gas filtration and decontamination system.

Example 1

General experimental: Chemically-modified cellulose (anionic cellulose) was prepared prior to the experimental procedure. Copper (II) acetate, 1,3,5-benzenetricarboxylic acid, methanol (MeOH), dimethylformamide (DMF), and ethanol (EtOH) were obtained from Sigma-Aldrich Company (St. Louis, Mo.). All chemicals and reagents used were analytical grade. The scanning electron microscopy (SEM) micrographs were recorded on a scanning electron microscopy (SEM, LEO 1550 FE-SEM) at 20 kV and the surfaces were carbon-coated before analysis. Powder X-ray diffraction patterns were collected with a Rigaku SmartLab X-Ray Diffractometer. Thermogravimetric analyses (TGA) were achieved using a thermal gravimetric analyzer from 30° C. to 600° C. under $N_2$. Fourier Transform Infrared (FT-IR) spectroscopy was carried out in a Nicolet Magna 760 FTIR spectrometer (Thermo Fisher Scientific Inc., Waltham, Mass.) at single attenuated total reflectance (ATR) mode. X-ray Photoelectron Spectroscopy (XPS) spectra were obtained on a Surface Science Instruments model SSX-I00, using a monochromated Al KR X-ray source.

Experimental Procedure

1. Synthesis of the metal-organic polyhedra (MOF 199) (HKUST-1) was carried out according to known procedures. For example, 1,3,5-Benzenetricarboxylic acid (500 mg, 2.38 mmol) was mixed in 12 mL of a 1:1:1 by volume mixture of DMF/EtOH/$H_2O$. Copper (II) acetate (860 mg, 4.31 mmol) was mixed with 12 mL of the same solvent and the mixtures combined with stirring. Triethylamine (0.5 mL) was added to the reaction mixture and stirred for 23 hours. The MOF was characterized by X-Ray Diffraction (XRD).

2. Chemical attachment of MOF to the anionic-modified cellulose (FIG. 1). For example, copper acetate was reacted with the carboxylate anion present in the anionic cellulose allowing in situ MOP synthesis. First, the modified cellulose was reacted with the copper acetate solution for 24 hours. Then, the in situ MOP synthesis takes place. After, the MOP blended anionic cellulose fiber was washed with water, dimethylformamide and methanol. Characterization was carried out by atomic force microscopy (AFM), scanning electron microscopy (SEM), field emission scanning electron microscopy (FESEM), X-Ray diffraction (XRD) and Thermogravimetric analysis (TGA).

Figure 2A:
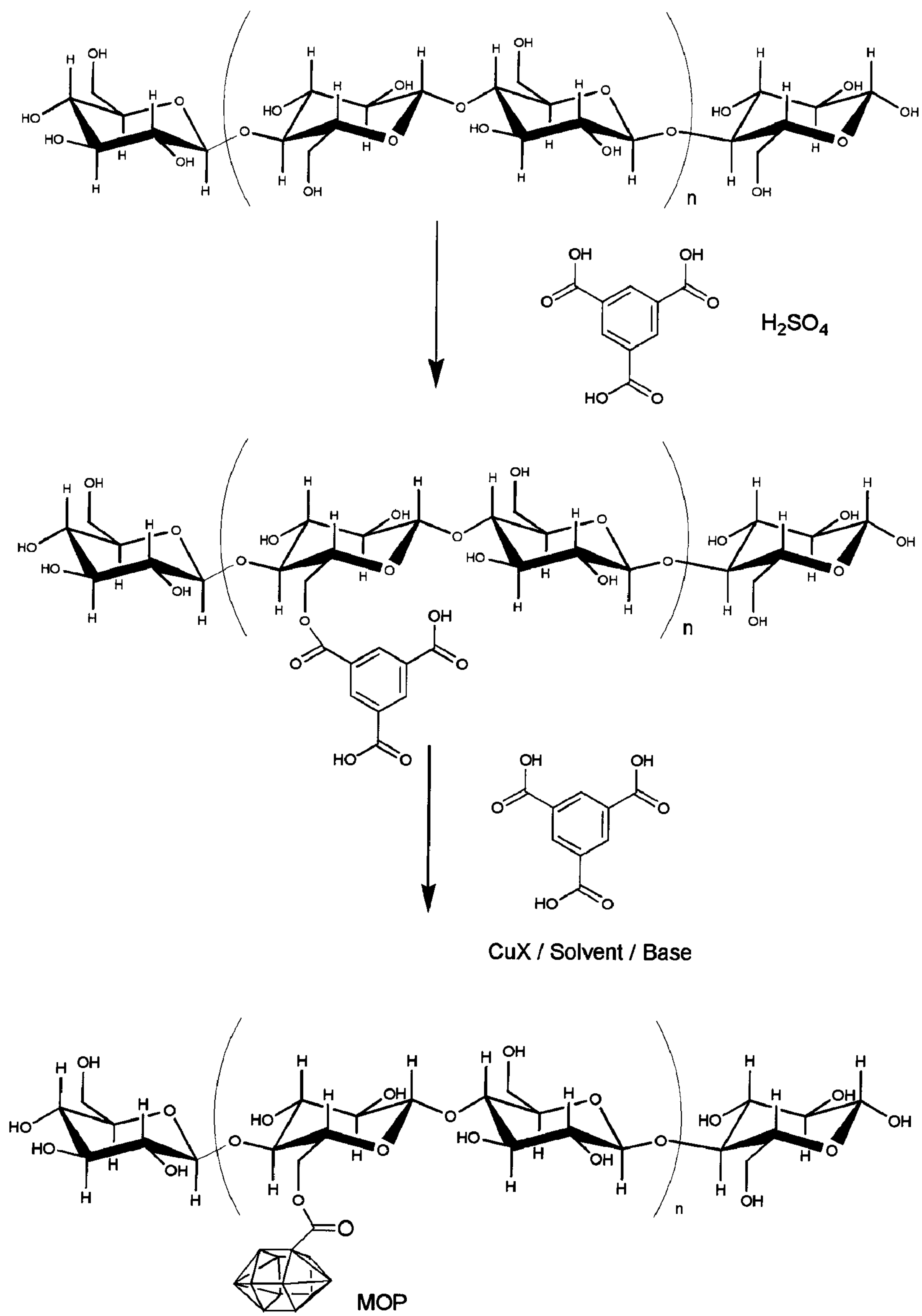
FIG. 2. Example of in situ formation of metal-organic framework ((A) an example of a MOP; and (B) an example of a MOF) chemically bonded to modified cellulose ester fibers. Where X represents the counterion for the copper salt.
Figure 2B:
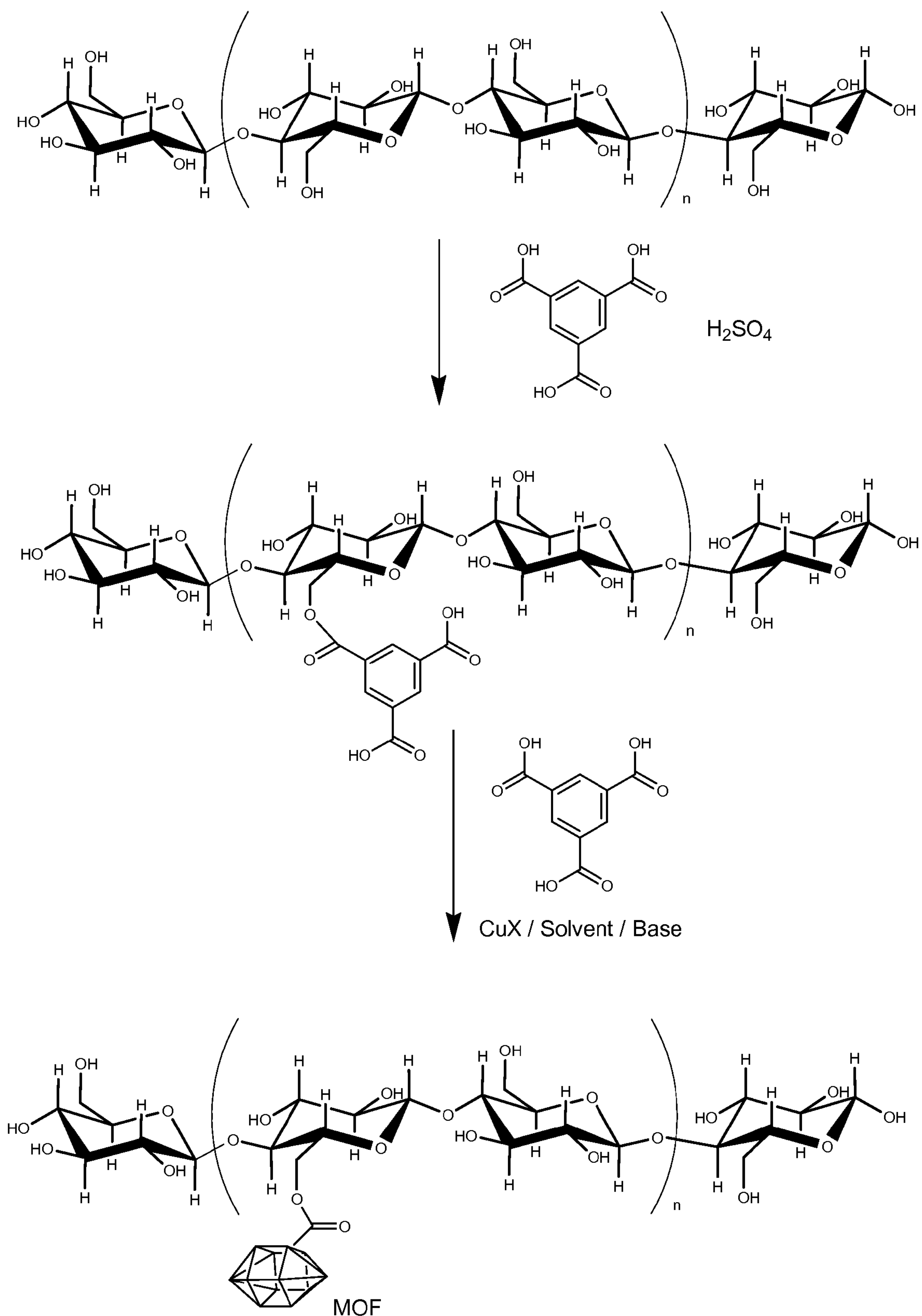
Figure 3:
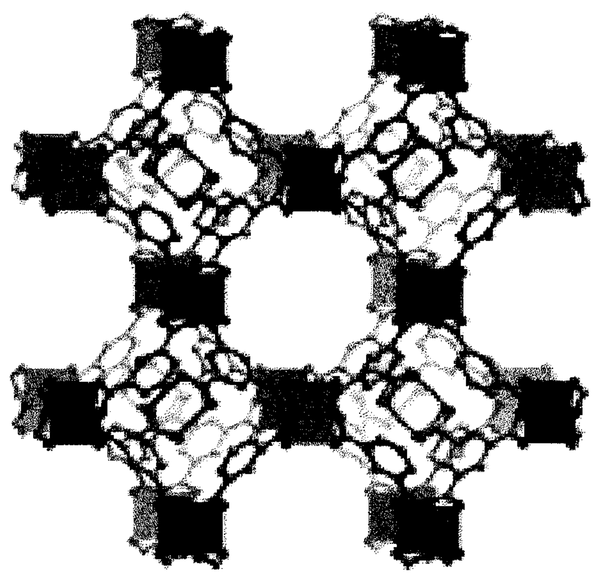
FIG. 3. Structure of MOF 199.

3. Chemical attachment of the MOF to unmodified cellulose (FIG. 2). Conditions: Cellulose and 1,3,5-Benzenetricarboxylic acid was mixed with dimethyl carbonate and concentrated sulfuric acid and heated under magnetic stirring at 80-85° C. for 8.5 hours. The reaction mixture was poured into 10% aq. sodium carbonate under stirring conditions. The ester cellulose formed was washed with dichloromethane and saturated sodium chloride, dried over sodium sulfate and the solvent evaporated. Copper (II) acetate solution (DMF:EtOH:$H_2O$, 1:1:1 by volume) was mixed with the ester cellulose allowing the MOP to be chemically attached to the fiber. Characterization was carried by atomic force microscopy (AFM), scanning electron microscopy (SEM), field emission scanning electron microscopy (FESEM), X-Ray diffraction (XRD) and Thermogravimetric analysis (TGA).

Example 2

Experiments

A—$Cu(OAc)_2$ (DMF/EtOH/$H_2O$), anionic cellulose
B—Anionic cellulose, $Cu(OAc)_2$ (DMF/EtOH/$H_2O$), 1,3,5-benzenetricarboxylic acid (DMF/EtOH/Water)
C—$Cu(OAc)_2$ (DMF/EtOH/$H_2O$), 1,3,5-benzenetricarboxylic acid (DMF/EtOH/$H_2O$), anionic cellulose
D—anionic cellulose, $Cu(OAc)_2$ (DMF/EtOH/$H_2O$) 1,3,5-benzenetricarboxylic acid (DMF/EtOH/$H_2O$)
Overnight/Stirring
A—1,3,5-Benzenetricarboxylic acid (DMF/EtOH/$H_2O$) and Triethylamine
B—Triethylamine
C—1,3,5-Benzenetricarboxylic acid (DMF/EtOH/$H_2O$)
D—No base
Washing:
Distilled $H_2O$
DMF
MeOH
5 hours stirring Chemical attachment of MOF 199 to the anionic-modified cellulose. The in situ synthesis of MOF 199 was performed following a modified known methodology. Different experimental procedures were performed to attach MOF 199 to the modified cellulose. A and C: Copper (II) acetate (860 mg) was mixed in 12 mL of a solvent mixture DMF:EtOH:$H_2O$ (1:1:1 by volume) and left overnight reacting with the anionic cellulose (0.17 g). Then, 1,3,5-benzenetricarboxylic acid (500 mg) previously dissolved in 12 mL of the same solvent mixture was added drop wise and keep stirring for another 24 hours. Then, for the experimental procedure A, 0.5 mL of triethylamine was added to the solution immediately after addition of 1,3,5-benzenetricarboxylic acid. B and D. Copper acetate (860 mg), 1,3,5-benzenetricarboxylic acid (500 mg) and anionic cellulose (0.17 g) were mixed in 12 mL of a solvent mixture DMF:EtOH:$H_2O$ (1:1:1 by volume) and left overnight under a vigorous stirring. Then, for the experimental procedure E, 0.5 mL of triethylamine was added to the solution immediately after addition of 1,3,5-benzenetricarboxylic acid. After that, the MOF 199 blended anionic cellulose fibers were washed for 3 hours with distilled $H_2O$, DMF and MeOH, respectively.

XRD patterns revealed the presence of MOF 199 onto anionic-modified fiber. The chemical attachment was confirmed by FTIR and XPS analyses. In addition, no difference on the temperature of degradation measured by TGA of these materials was observed, suggesting that the properties were preserved.

Example 3

Experiment A: Copper (II) acetate (860 mg) was mixed in 12 mL of a solvent mixture of DMF:EtOH:$H_2O$ (1:1:1 by volume) and left overnight reacting with the anionic cellulose (0.17 g). Then, 1,3,5-benzenetricarboxylic acid (500 mg) previously dissolved in 12 mL of the same solvent mixture was added dropwise, followed immediately by 0.5 mL of triethylamine and stirred for another 5-24 hours when the MOF 199 blended anionic cellulose fibers were washed for 3 hours with $H_2O$, DMF, and MeOH respectively.

Example 4

Experiment B: Copper (II) acetate (860 mg), 1,3,5-benzenetricarboxylic acid (500 mg) and anionic cellulose (0.17 g) were mixed in 12 mL of a solvent mixture DMF:EtOH:$H_2O$ (1:1:1 by volume) and left overnight with vigorous stirring. Then, 0.5 mL of triethylamine was added to the solution and stirred for another 5-24 hours when the MOF 199 blended anionic cellulose fibers were washed for 3 hours with $H_2O$, DMF, and MeOH respectively.

Example 5

Experiment C: Copper (II) acetate (860 mg) was mixed in 12 mL of a solvent mixture of DMF:EtOH:$H_2O$ (1:1:1 by volume) and left overnight reacting with the anionic cellulose (0.17 g). Then, 1,3,5-benzenetricarboxylic acid (500 mg) previously dissolved in 12 mL of the same solvent mixture was added dropwise and stirred for another 5-24 hours when the MOF 199 blended anionic cellulose fibers were washed for 3 hours with $H_2O$, DMF, and MeOH respectively.

Example 6

Experiment D: Copper (II) acetate (860 mg), 1,3,5-benzenetricarboxylic acid (500 mg) and anionic cellulose (0.17 g) were mixed in 12 mL of a solvent mixture DMF:EtOH:$H_2O$ (1:1:1 by volume) and left overnight under a vigorous stirring and stirred an additional 5-24 hours when the MOF 199 blended anionic cellulose fibers were washed for 3 hours with $H_2O$, DMF, and MeOH respectively.

Example 7

Chemical attachment of the MOF to unmodified cellulose: Cellulose and 1,3,5-Benzenetricarboxylic acid will be mixed with dimethyl carbonate and conc. sulfuric acid and heated under magnetic stirring at 80-85° C. for 8.5 hours. The reaction mixture will be poured into 10% aq. sodium carbonate under stirring. The ester cellulose formed will be washed with dichloromethane and sat. sodium chloride, dried over sodium sulfate and the solvent evaporated. Copper (II) acetate solution (DMF:EtOH:$H_2O$, 1:1:1, by volume) will be mixed with the ester cellulose allowing the MOF to be chemically attached to the fiber.

Example 8

Zirconium oxide nanofiber preparation: Granular polyvinyl pyrrolidone (PVP, average molecular weight 1.3×106, Sigma Aldrich, St Louis, Mo., USA) was used as the polymeric component of all the composites fabricated in this study. The polymeric solution was made by dissolving the PVP granular powder in reagent grade DMF/$CH_2Cl_2$ in 3:1 ratio under constant and vigorous stirring to give 12% wt. PVP solution. This concentration was arrived at and selected after several preliminary iterations with respect to the desired viscosity of the inorganic-organic composite solutions were carried out. Zirconia nanofibers were prepared according to an electrospinning in combination with sol-gel process and subsequently calcination with a slight modification. The spinning solutions were first prepared by mixing 1 mL of zirconium propoxide in 12% PVP, followed by addition of 0.5 ml acetyl acetone to stabilize the alkoxide. The resulting mixture was continuously stirred for 1 h. The flow rate of the spinning solutions ranged from 15-50 μL/hour, controlled by syringe pump. In all of the experiments, the applied voltage was maintained at 20 kV. A grounded metal screen covered by an aluminum foil was used as the counter electrode and was placed 20 cm from the tip of the capillary. As the jet accelerated towards the collector, the solvent evaporated, leaving only ultrathin fibers on the collector. Continuous fibers were deposited and collected in the form of fibrous nonwoven mats. Subsequently, calcination at 550° C. for 3 hours was also carried out for each sample after electrospinning. The morphology of the resulting nanofibers was studied using LEO 1550 FESEM (Keck SEM). Powder X-ray diffraction (XRD) measurements were performed on a Scintag Theta-Theta X-ray Diffractometer (PAD-X) with Ni-filtered Cu Kα radiation (λ=1.54178 Å). For all samples, XRD spectra were obtained by scanning over 2θ angles of 20-80° at scanning speed of 2°/min and step width of 0.02°.

Example 9

Attachment of MOF 199 to modified zirconium oxide fibers: Zirconium oxide nanofibers were functionalized with tetrachlorosilane ($SiCl_4$) in water in order to generate hydroxyl terminated silane groups on the surface. The created hydroxyl groups were used to create an anchor for attachment of MOF 199 on the $ZrO_2$ nanofibers. Carboxymethylation reaction on $ZrO_2$ fibers were carried out using 1 M sodium chloroacetate and 5% sodium hydroxide and the reaction allowed to proceed for 1 hour. Carboxymethylated $ZrO_2$ fibers were washed with de-ionized water several times to completely remove unreacted reagents. MOF 199 was synthesized in-situ by mixing a solution of Copper (II) nitrate (2.07 g) in de-ionized water (20 ml) with a solution of 1,3,5-benzene tricarboxylic acid (1.0 g) in EtOH/DMF solvent mixture in 1:1 ratio (40 ml). The carboxymethylated zirconium oxide nanofibers were first immersed in copper nitrate solution for 2 hours before adding 1,3,5-benzene tricarboxylic acid solution dropwise with gentle stirring. Triethyl amine (1.0 ml) was immediately added to the solution after the addition of 1,3,5-benzenetricarboxylic and was left stirring for 24 hours. The blue product was filtered out and washed thoroughly with a mixture of $H_2O$:EtOH (1:1).

Example 10

Attachment of MOF 199 to polyacrylonitrile (PAN) fibers: Polyacrylonitrile (PAN) nanofibers were prepared by electrospinning of a 14% PAN solution. The spinning solutions were first prepared by mixing PAN powder in dimethyl-N'N-formamide (DMF) solvent for 12 hours in order to obtain 14% solution. The flow rate of the spinning solutions ranged from 15-50 μL/hour, controlled by syringe pump. In all of the experiments, the applied voltage was maintained at 20 kV. A grounded metal screen covered by an aluminum foil was used as the counter electrode and was placed 20 cm from the tip of the capillary. As the jet accelerated towards the collector, the solvent evaporated, leaving only ultrathin fibers on the collector. Collected fibers were peeled off aluminum foil for further processing. MOF-199 was synthesized in situ by mixing a solution of Copper (II) nitrate (2.07 g) in de-ionized $H_2O$ (20 ml) with a solution of 1,3,5-benzene tricarboxylic acid (1.0 g) in EtOH/DMF solvent mixture in 1:1 ratio (40 ml). First, the electrospun PAN fiber was reacted with the copper acetate solution for 2 hours. Then, in situ MOF synthesis was conducted by adding 1,3,5-benzene tricarboxylic acid solution dropwise with gentle stirring. Triethyl amine (1.0 ml) was immediately added to the solution after the addition of 1,3,5-benzenetricarboxylic and was left stirring for 24 hours. After, the MOF blended PAN fiber was filtered out and washed with $H_2O$:EtOH (1:1). Characterization was carried out by field emission scanning electron microscopy (FESEM) and Thermogravimetric analysis (TGA).

Example 11

Characterization of Anionic Modified Cellulose with MOP 199

Table 1 shows the elemental surface composition (in %) determined by XPS of anionic-modified cellulose after in situ synthesis of MOF 199 following different experimental procedures. It was observed that the experiments A and C had similar copper concentrations (0.49 and 0.54, respectively). XPS analysis of one the samples (Experiment B) was performed for matter of comparison. As expected, the copper concentration was much smaller (0.25) than from the Experiments A and C, indicating that in this case probably just copper acetate was attached to the anionic-modified cellulose during the in situ synthesis.

TABLE 1

| Experimental | Elemental compositions (%) | | |
|---|---|---|---|
| procedures | O1s | C1s | Cu2p |
| A | 39.22 | 60.29 | 0.49 |
| B | 39.18 | 60.57 | 0.25 |
| C | 37.29 | 62.17 | 0.54 |

Figure 4:
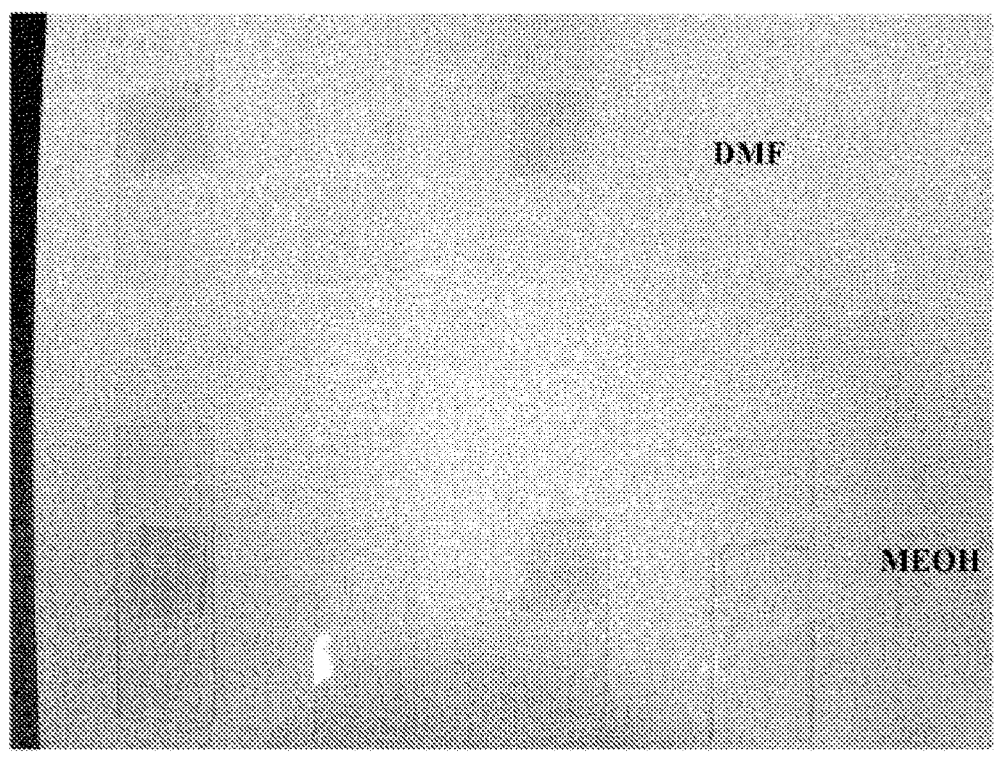
FIG. 4. An optical photograph of an example of anionic cellulose after water, DMF, and methanol washing treatments.

FIG. 4 shows the resulting fabrics after performing different experimental procedures and successive washing treatments. Experiments B and D had a light blue shade. Experiments A and C resulted in the darkest blue cellulose. The turquoise-blue cellulose is expected in the samples that have successfully attached the MOF 199 since this is the normal color for MOF 199 crystals.

Figure 5:
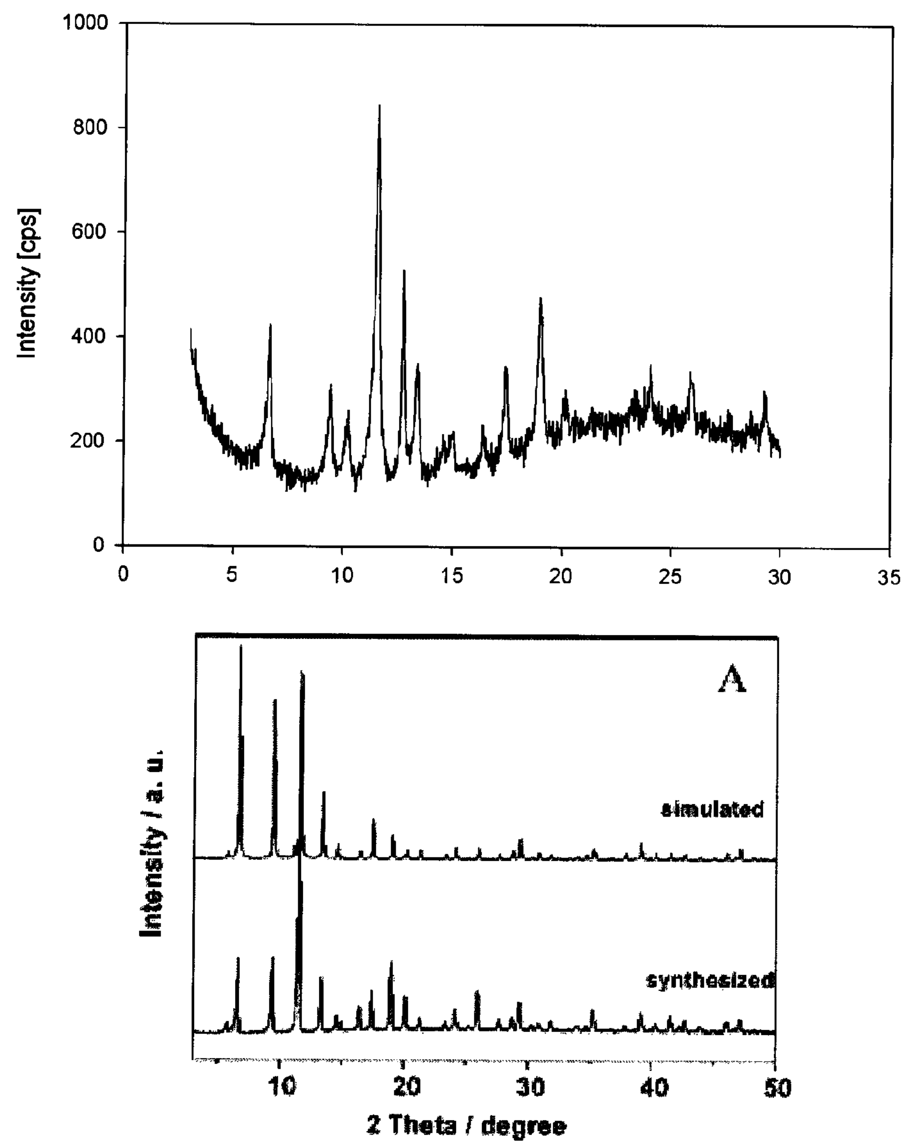
FIG. 5. XRD pattern of MOF 199 prepared using 1,3,5-benzenetricarboxylic acid.
Figure 6:
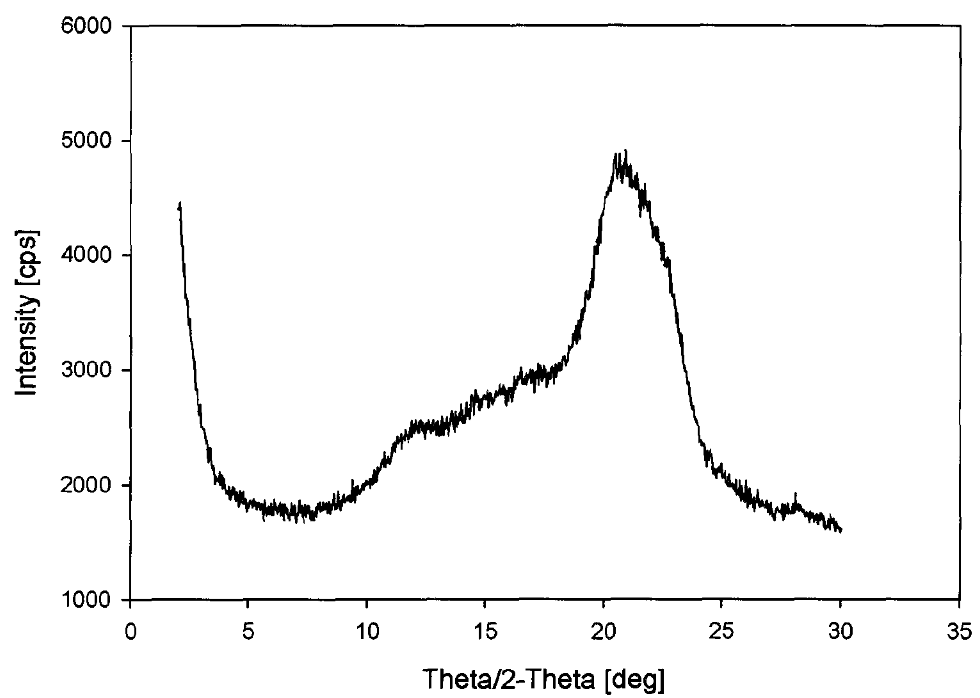
FIG. 6. XRD pattern of an example of anionic cellulose.
Figure 7:
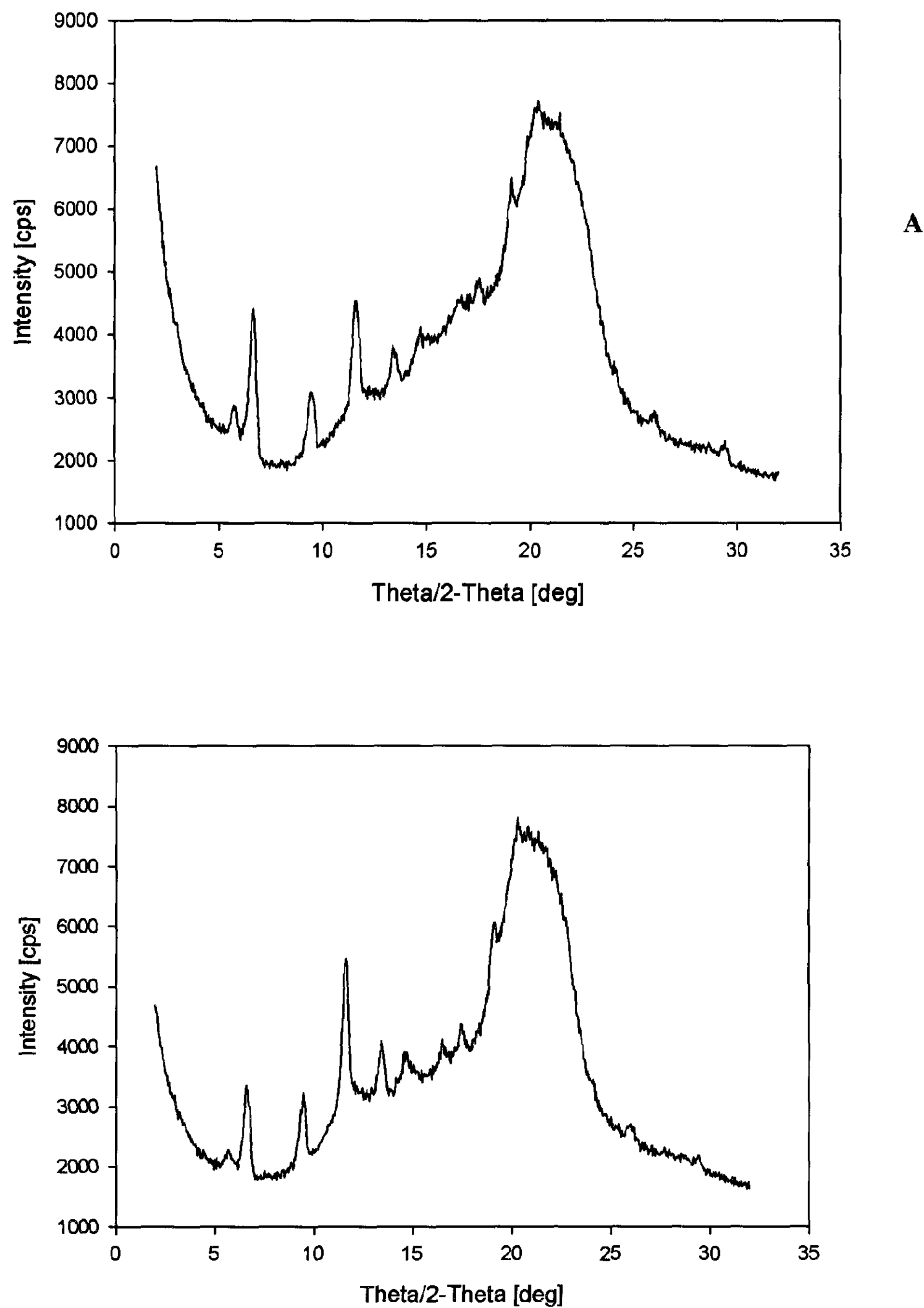
FIG. 7. XRD pattern of anionic cellulose from experiment A after DMF (A) and MeOH (B) treatments.
Figure 8:
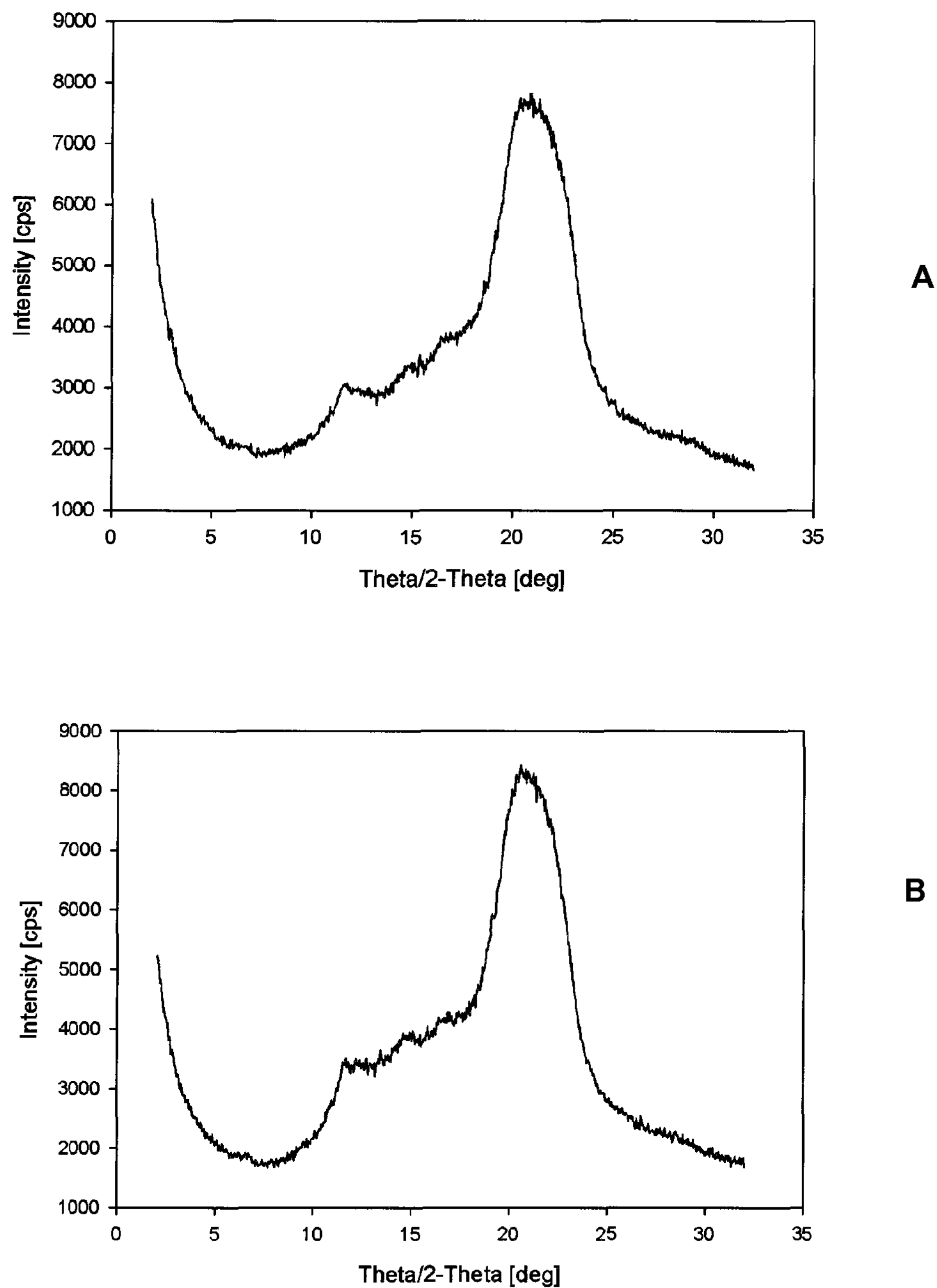
FIG. 8. XRD pattern of anionic cellulose from experiment B after DMF (A) and MeOH (B) treatments.
Figure 9:
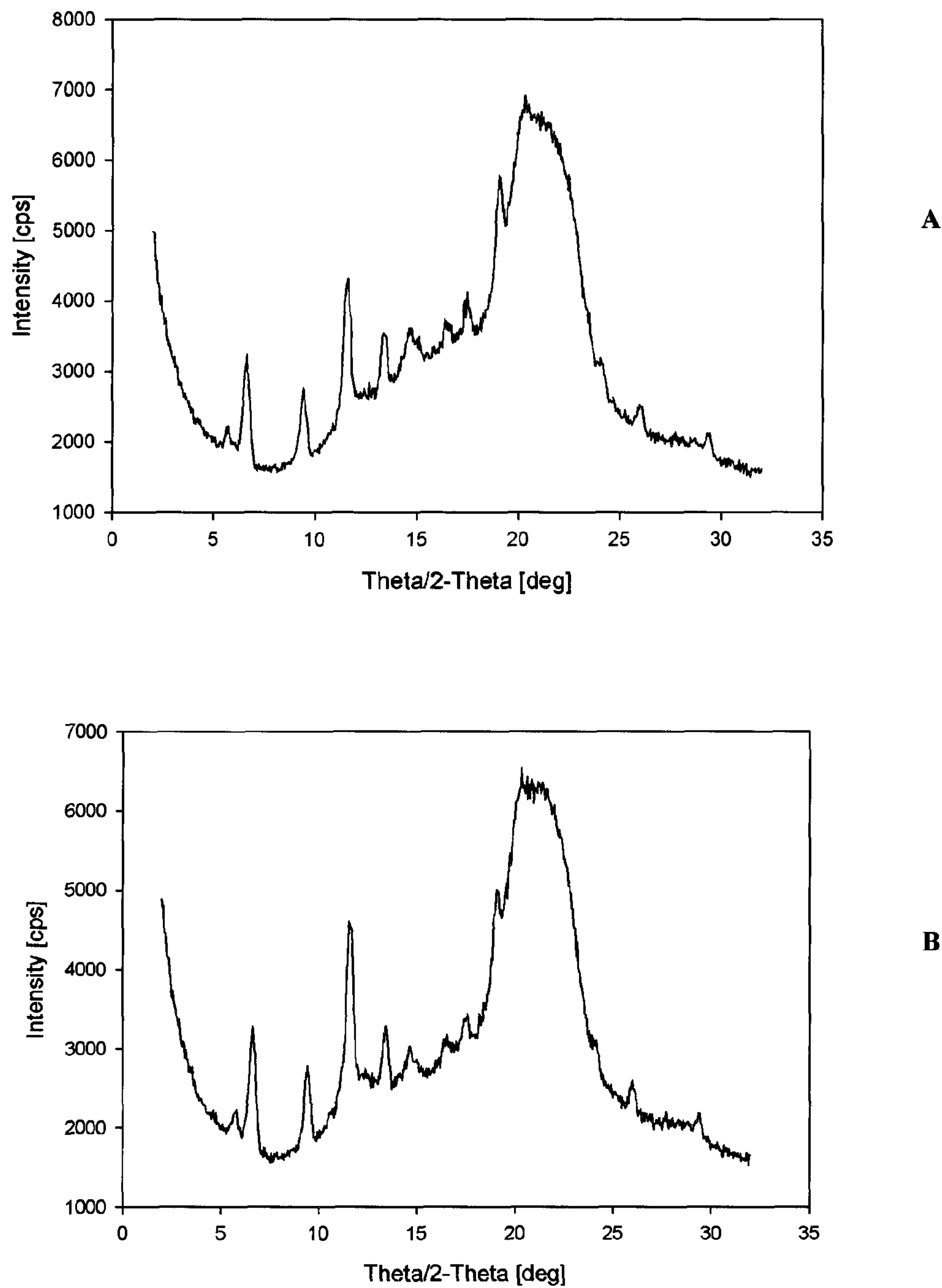
FIG. 9. XRD pattern of anionic cellulose from experiment C after DMF (A) and MeOH (B) treatments.
Figure 10:
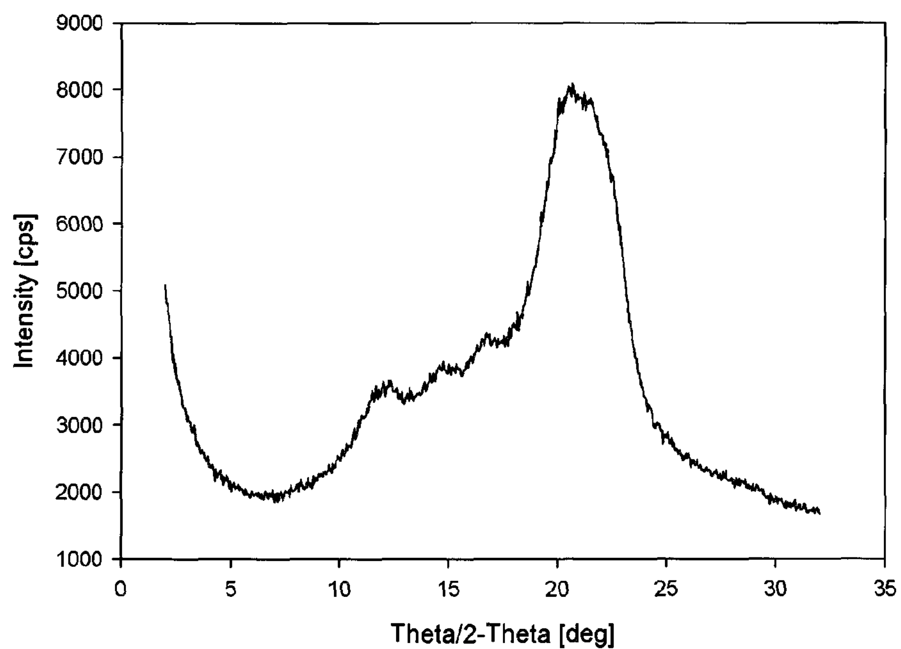
FIG. 10. XRD pattern of anionic cellulose from experiment D after MeOH treatments.

FIG. 5 shows the XRD pattern of isolated MOF 199. The peaks corresponding to MOF 199 are in accordance with the literature. FIG. 6 shows the XRD pattern of the anionic cellulose before in situ synthesis of MOF 199. FIGS. 7-10 show the XRD pattern of the anionic cellulose after in situ synthesis of MOF 199 onto the anionic-modified cellulose according to experiments A-D respectively. The results indicated that only experiments A and C peaks corresponding to the crystals of MOF 199 were detected.

Figure 11:
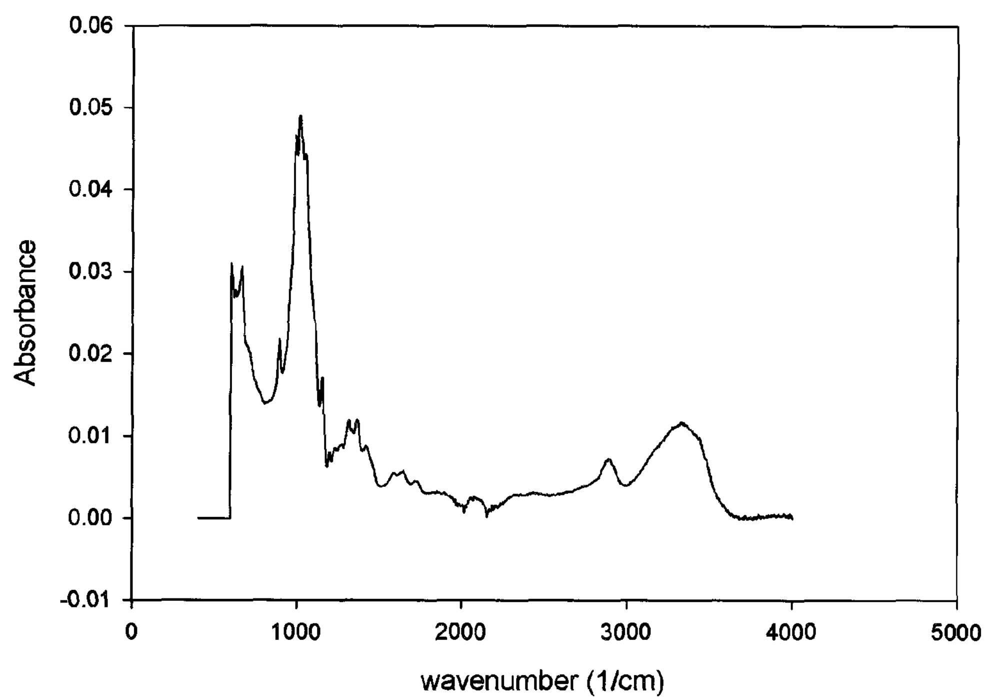
FIG. 11. FT-IR spectrum of an example of anionic cellulose.
Figure 12:
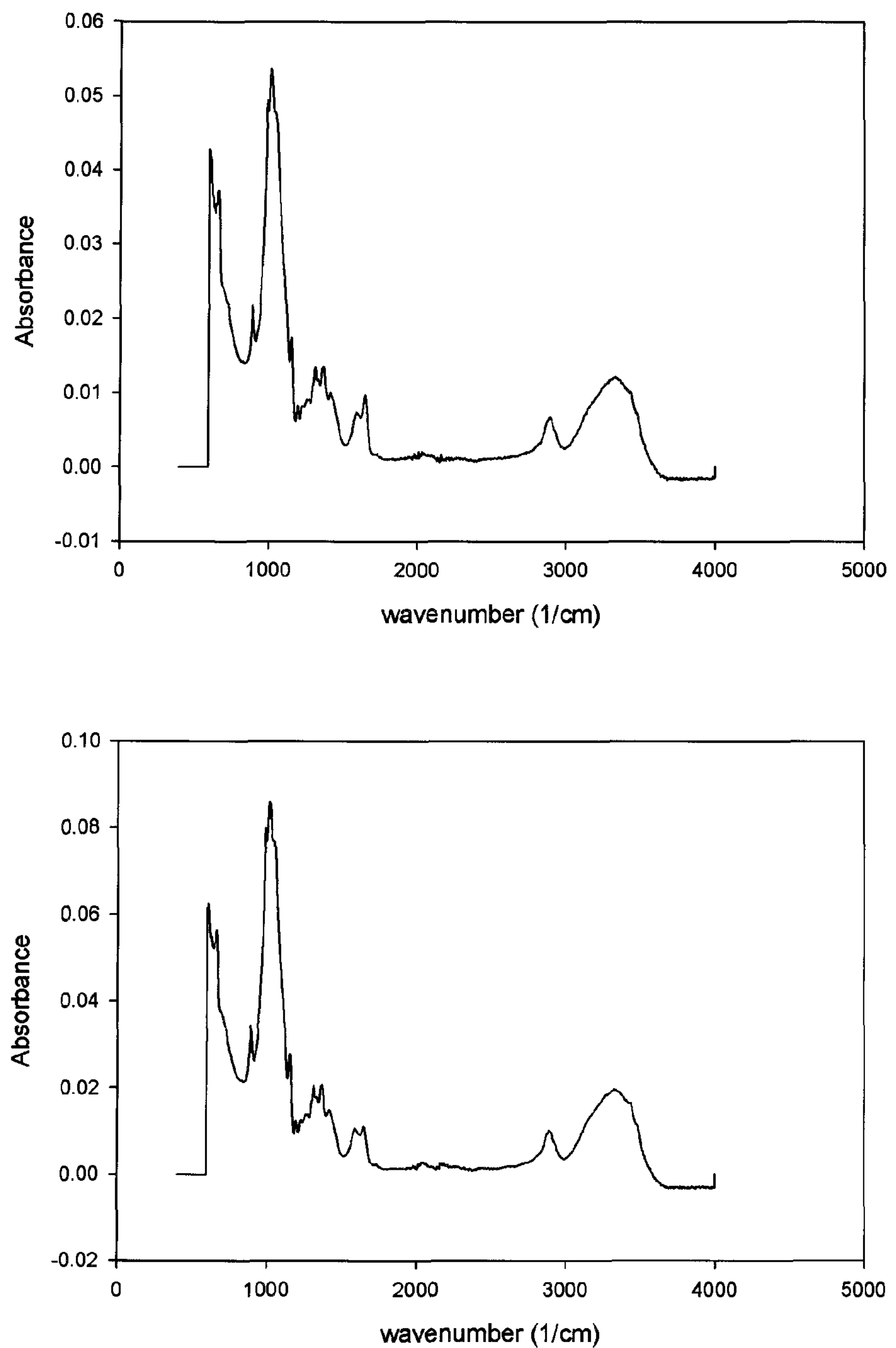
FIG. 12. FT-IR spectra of anionic cellulose from experiment A after treatment with DMF (A) and MeOH (B).
Figure 13:
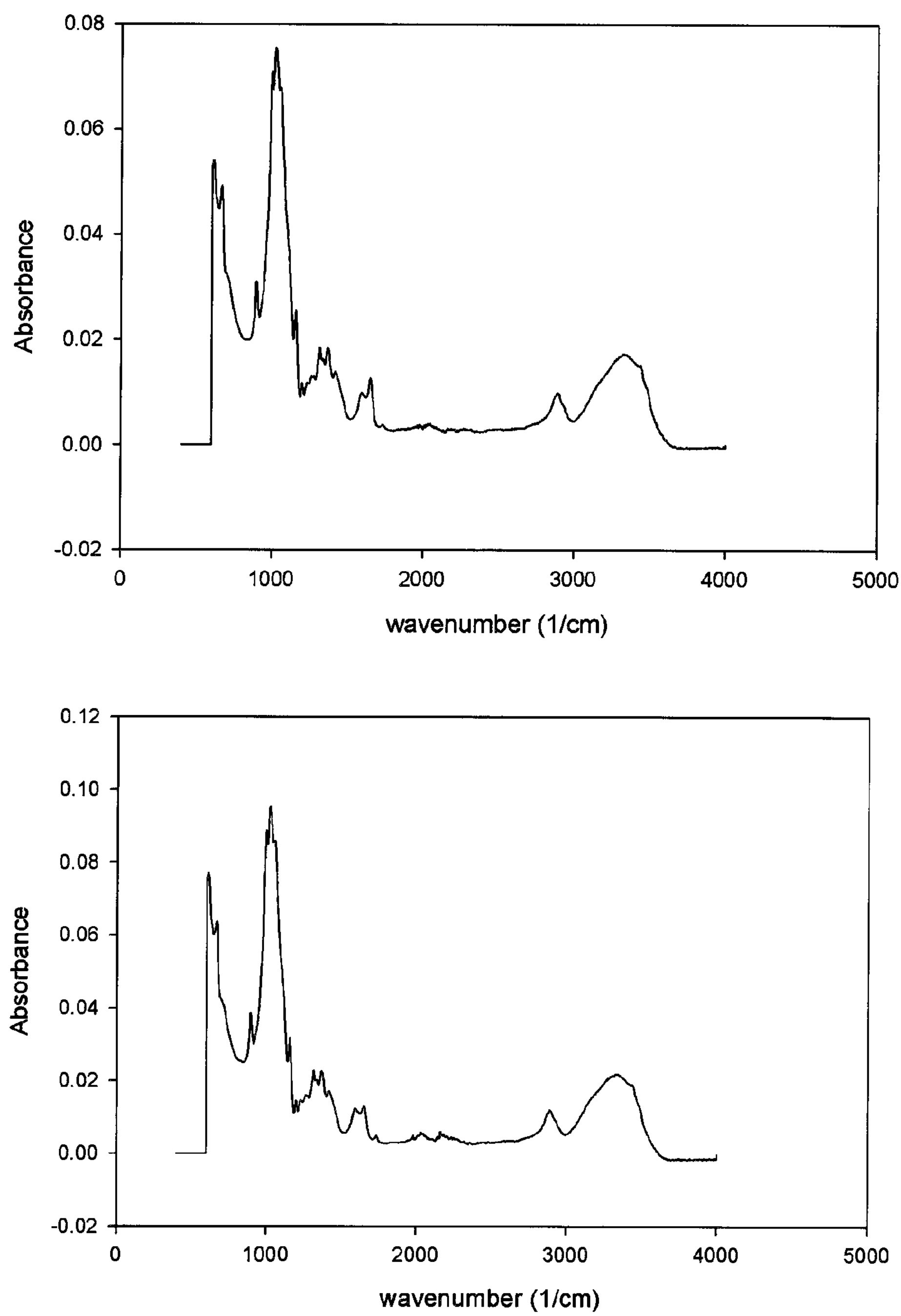
FIG. 13. FT-IR spectra of anionic cellulose from experiment B after treatment with DMF (A) and MeOH (B).
Figure 14:
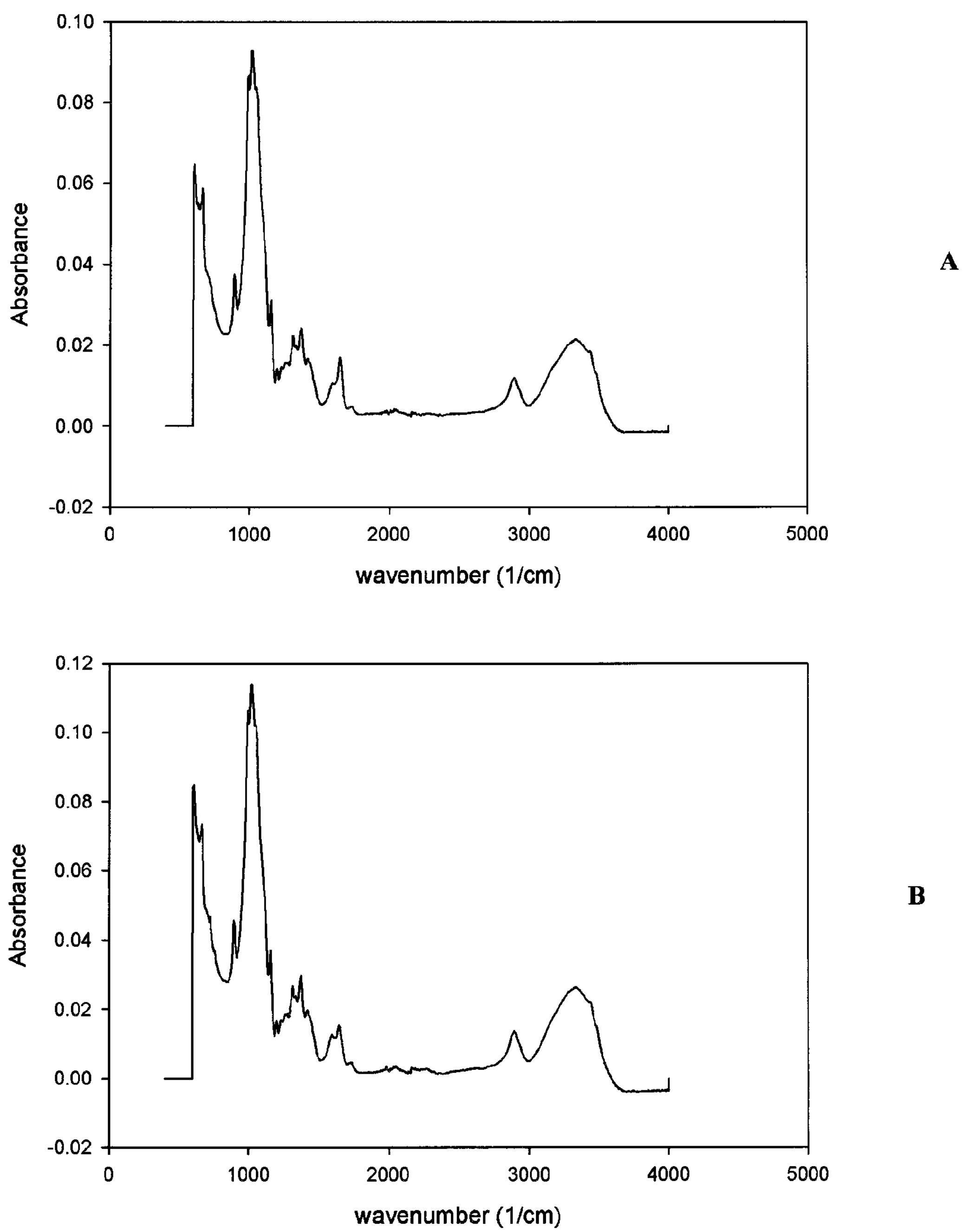
FIG. 14. FT-IR spectra of anionic cellulose from experiment C after treatment with DMF (A) and MeOH (B).
Figure 15:
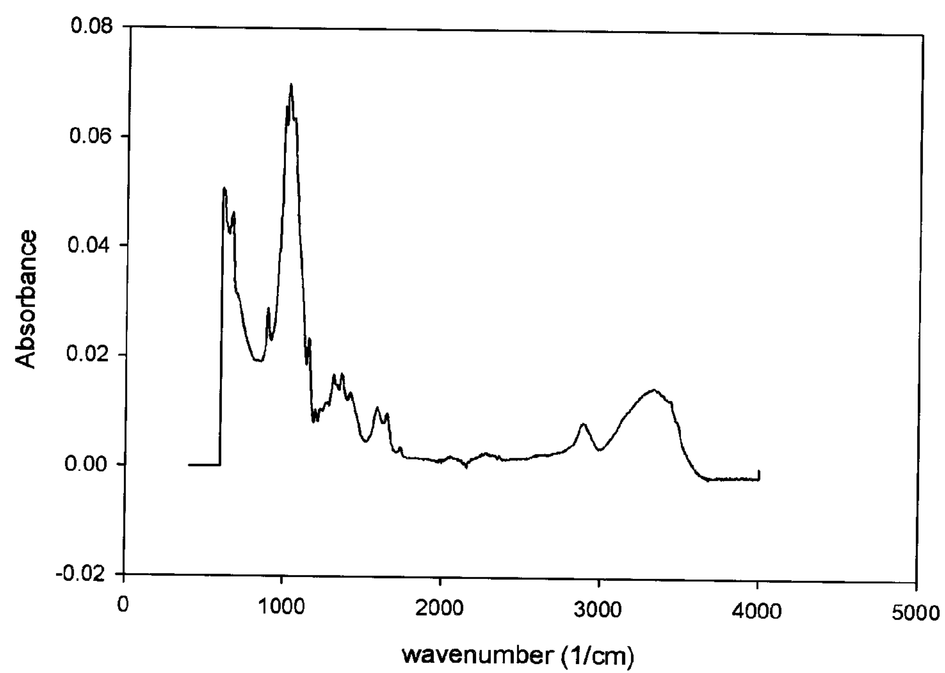
FIG. 15. FT-IR spectra of anionic cellulose from experiment D after treatment with DMF and MeOH, respectively.

FIG. 11 shows an FTIR spectra of an example of anionic cellulose. FIGS. 12-15 show the change in the FTIR spectra of experiments A-D respectively to that of the anionic-modified cellulose.

Figure 16:
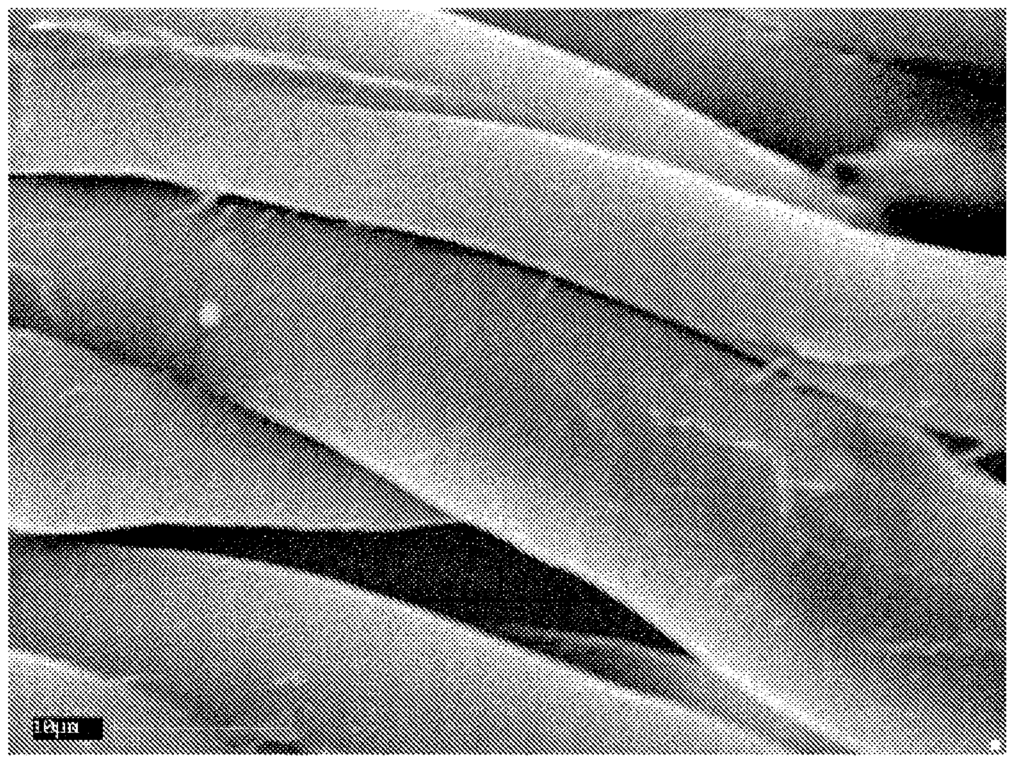
FIG. 16. SEM image of an example of anionic cellulose (without treatment).
Figure 17:
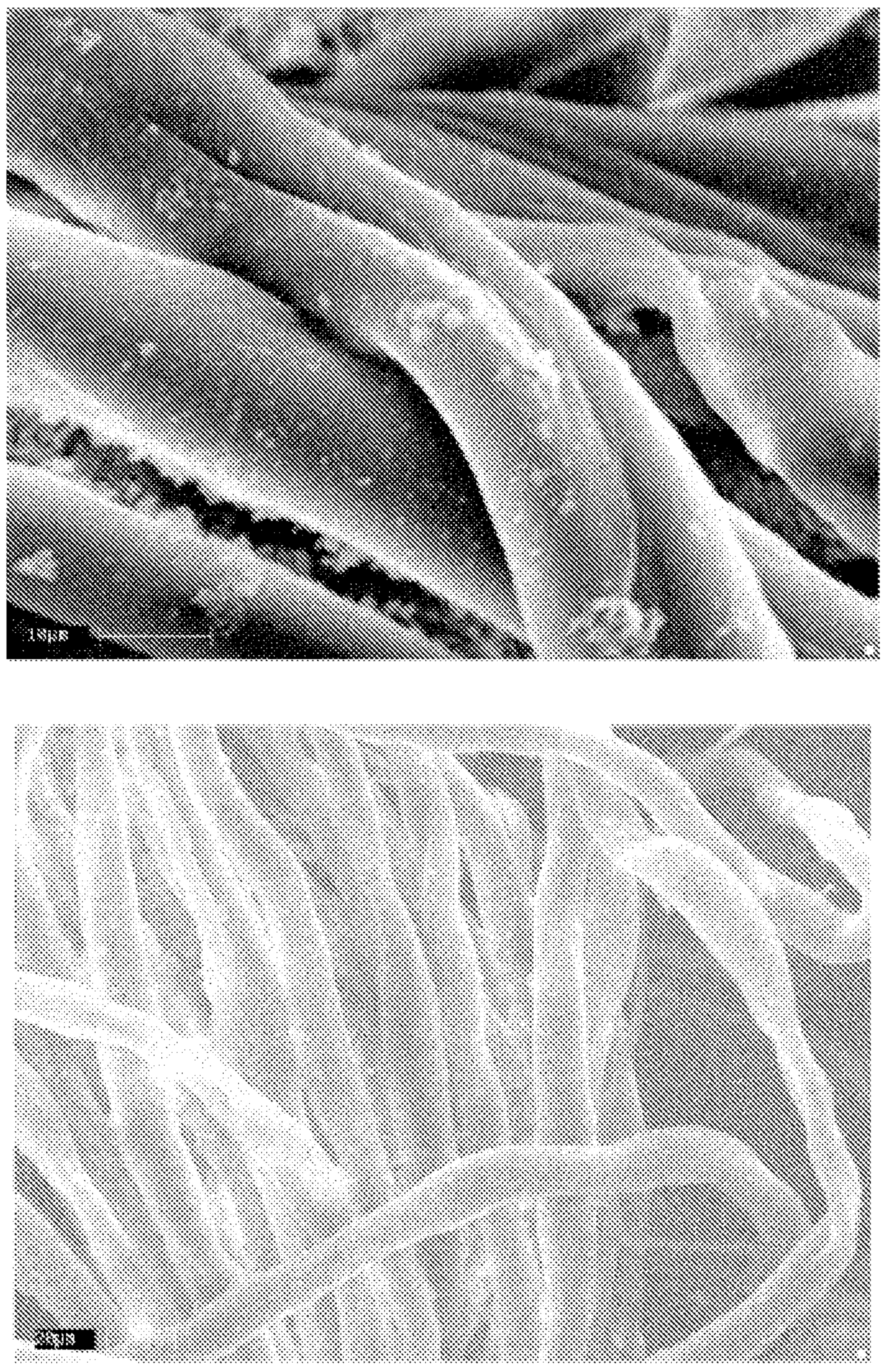
FIG. 17. SEM images of anionic cellulose from the experiment A after treatment with DMF (A) and MeOH (B).
Figure 18:
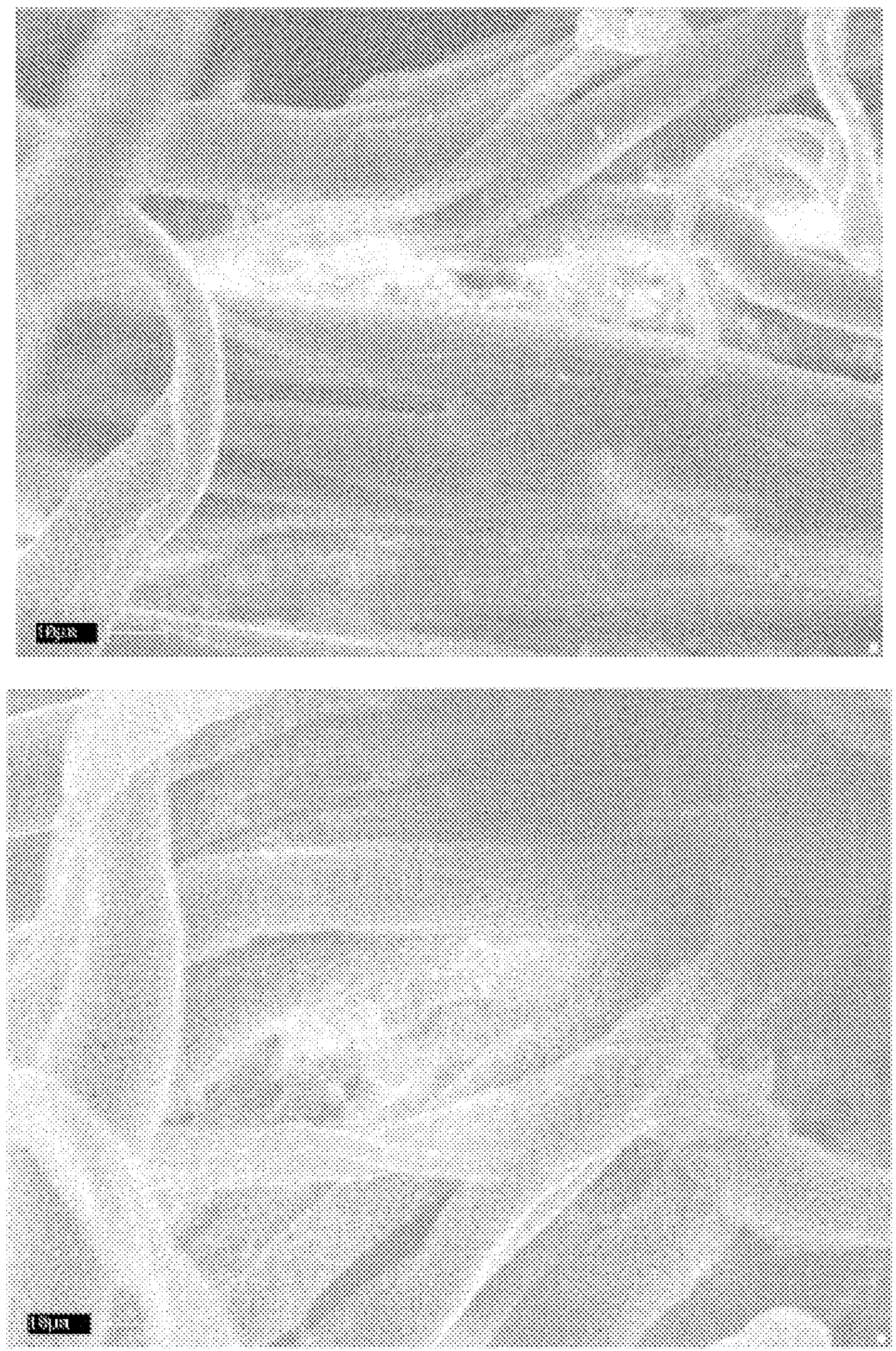
FIG. 18. SEM images of anionic cellulose from experiment C after treatment with DMF (A) and MeOH (B).
Figure 19:
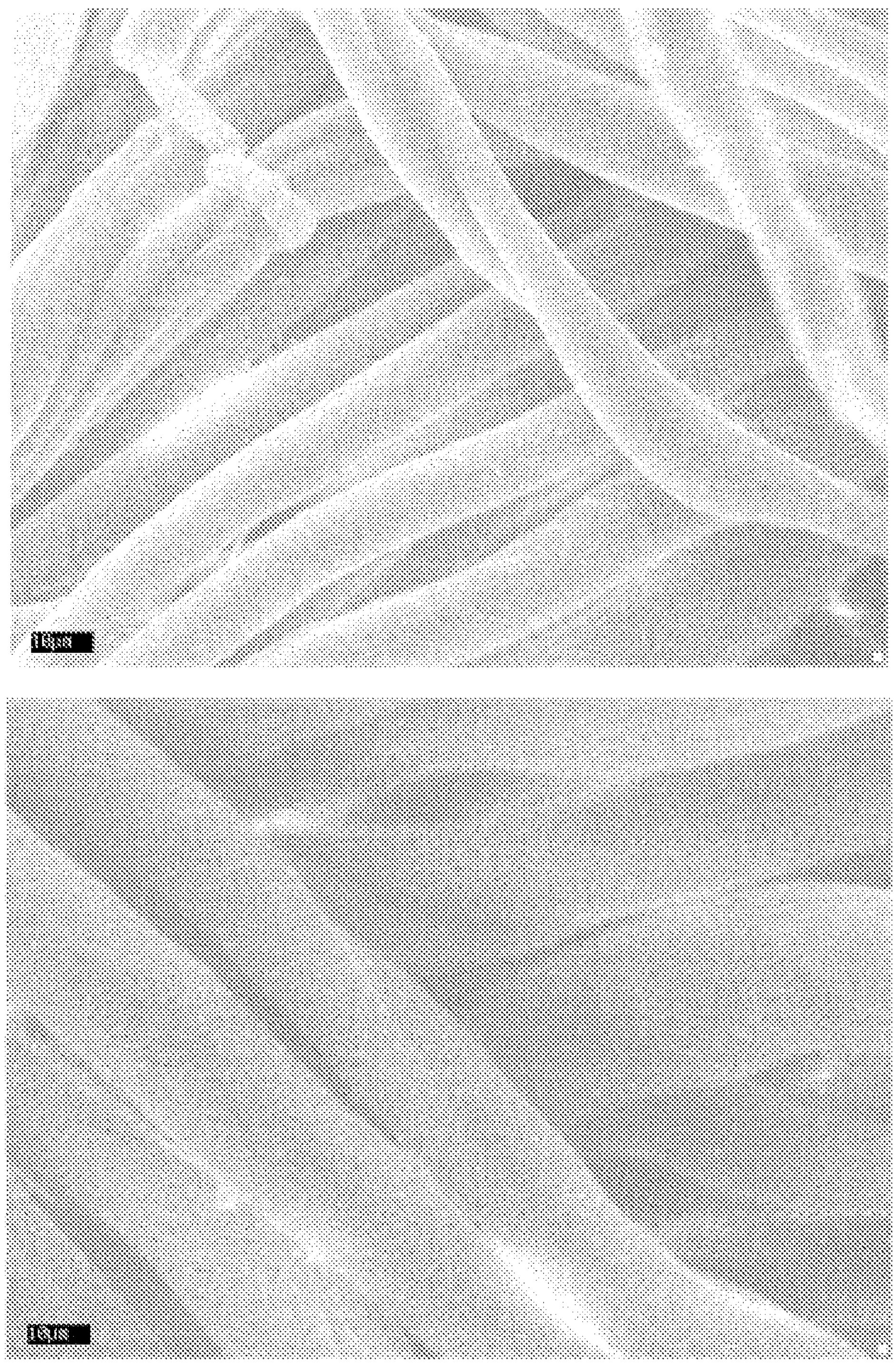
FIG. 19. SEM images of anionic cellulose from experiment B (a) and D (b) after treatment with MeOH.
Figure 20:
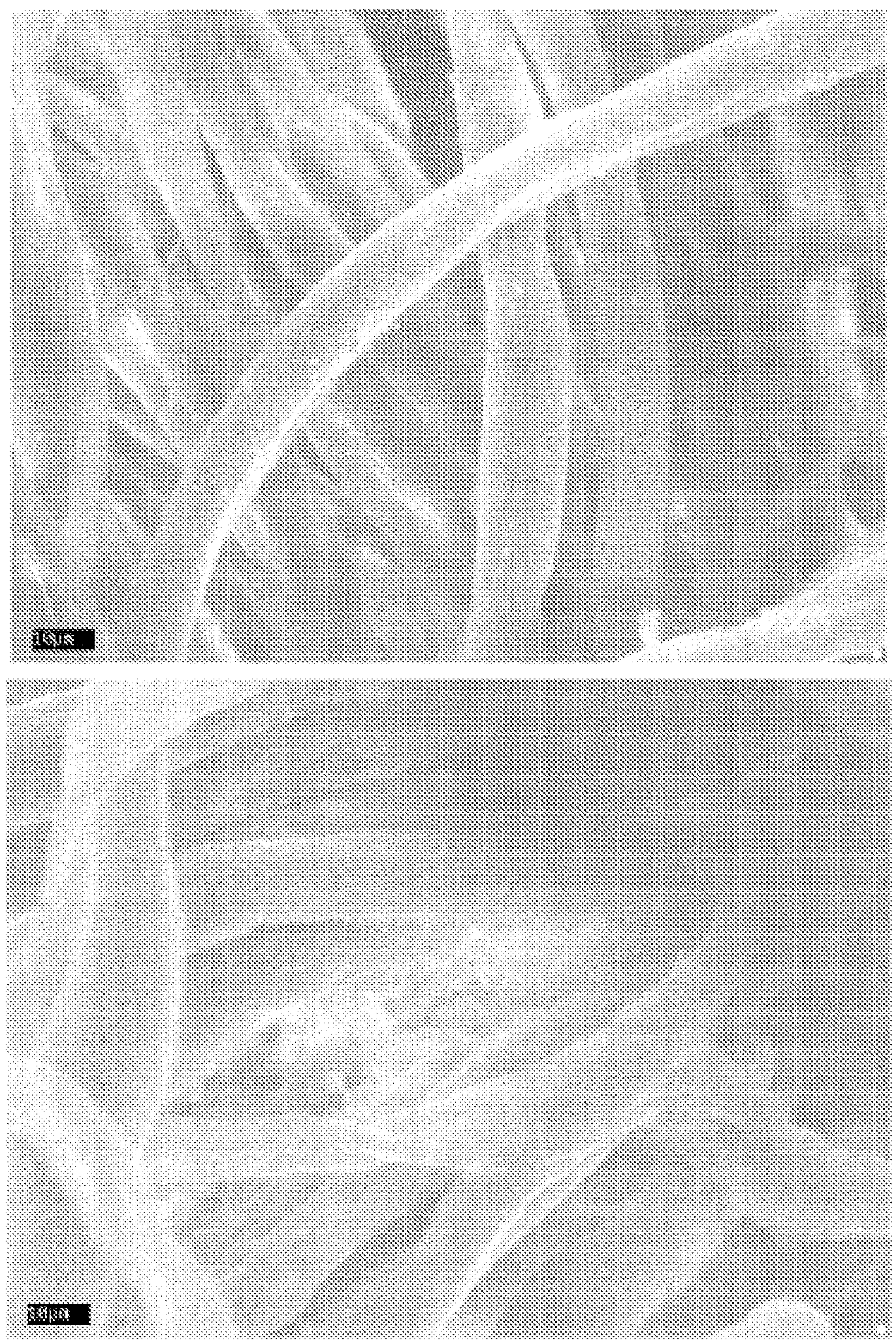
FIG. 20. SEM images of anionic cellulose from experiment A (a) and C (b) after treatment with MeOH.

FIG. 16 shows a SEM image of an example of anionic-modified cellulose without treatment to show the surface morphology before chemical attachment of the MOF 199. FIG. 17 shows SEM images of anionic cellulose from experiment A. FIG. 18 shows SEM imaging from experiment C of the anionic cellulose. FIG. 19 shows SEM imaging of anionic cellulose from experiments B and D respectively. FIG. 20 shows the comparison of the SEM images from experiments A and C.

Figure 21:
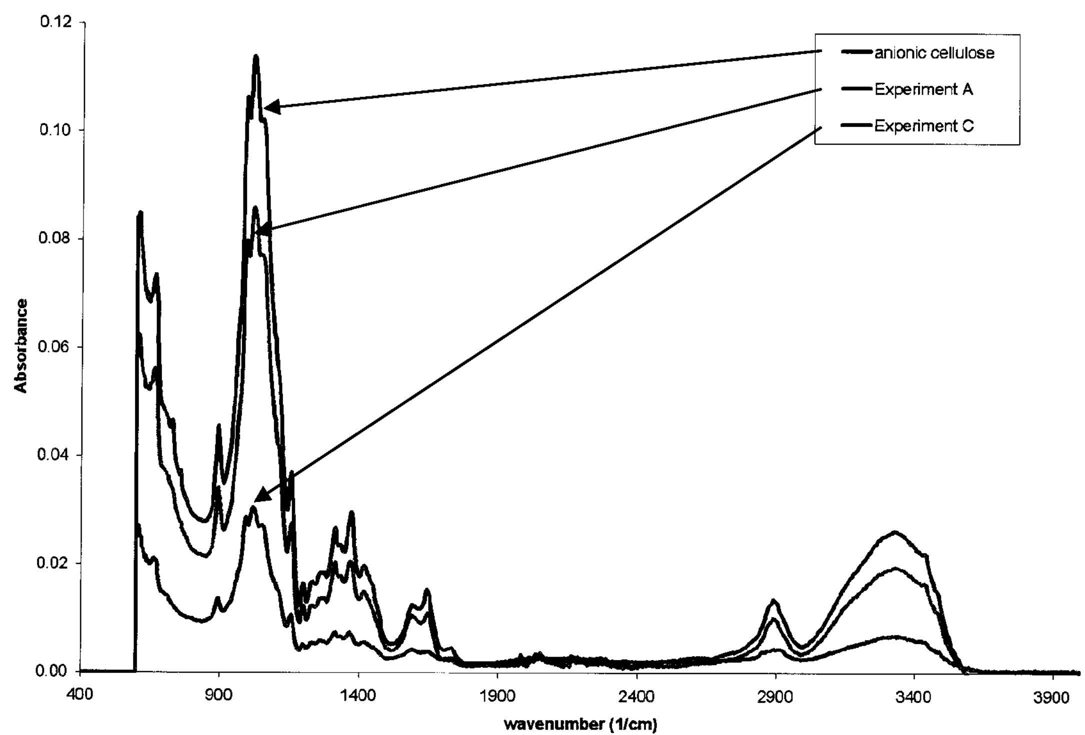
FIG. 21. FTIR Spectra of the anionic-modified cellulose before and after in situ synthesis of MOF 199 from the different experimental procedures (A and C)
Figure 22:
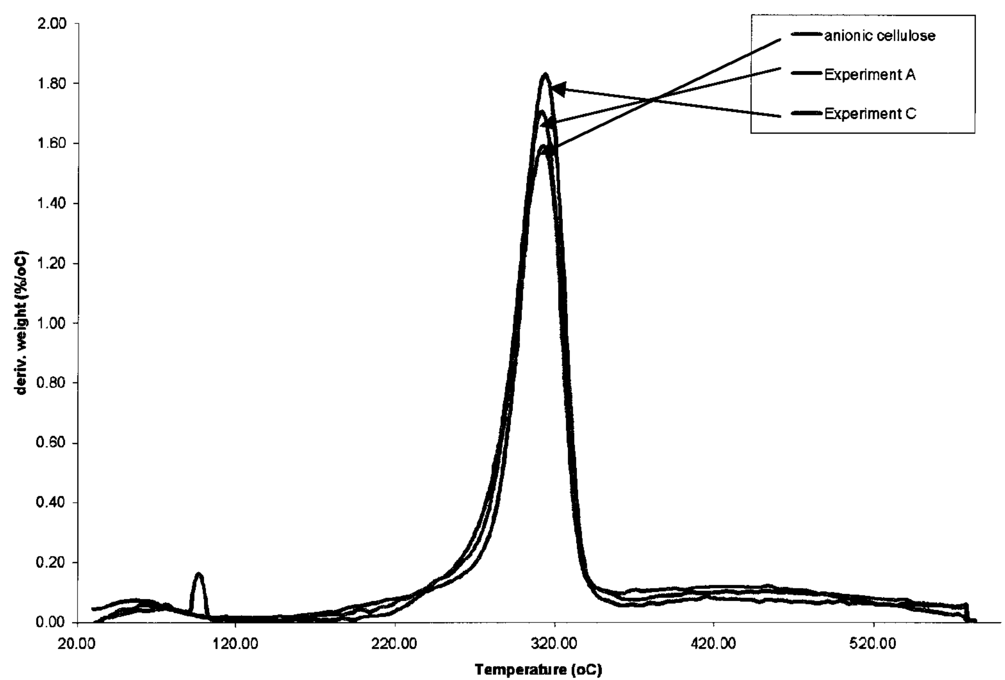
FIG. 22. An example of thermogravimetric analyses (TGA) of anionic-modified cellulose before and after in situ synthesis of MOF 199.

FIG. 21 shows FTIR analysis according to the present disclosure of experiments A and C at ATR mode of the surface chemical structures from anionic-modified cellulose before and after in situ synthesis of MOF 199 following the experiments A and C. From FT-IR analyses, it was observed strong hydrogen-bonded OH stretching at 3325 $cm^{-1}$ and CH stretching mode at 2891 $cm^{-1}$. In addition, there was a significant change in the region of 1600 corresponding to the carboxylate groups present in the anionic-modified cellulose before in situ synthesis of MOF 199. 1723 $cm^{-1}$ increases due to the stretching of carbonyl group FIG. 22 shows the thermogravimetric analysis (TGA) of the present disclosure of experiments A and C. TGA was performed to evaluate the possible changes on the temperature degradation after chemical attachment of MOP 199 to the surface of the anionic-modified cellulose. It has been previously reported that MOF 199 crystals were stable at up to a temperature of about 400° C. However, it has also been reported that MOF 199 is stable up to 240° C. No significant difference on the temperature of degradation was observed for the experiments A and C when compared to the anionic-modified cellulose before in situ synthesis, indicating that original properties of the material were preserved.

Figure 23:
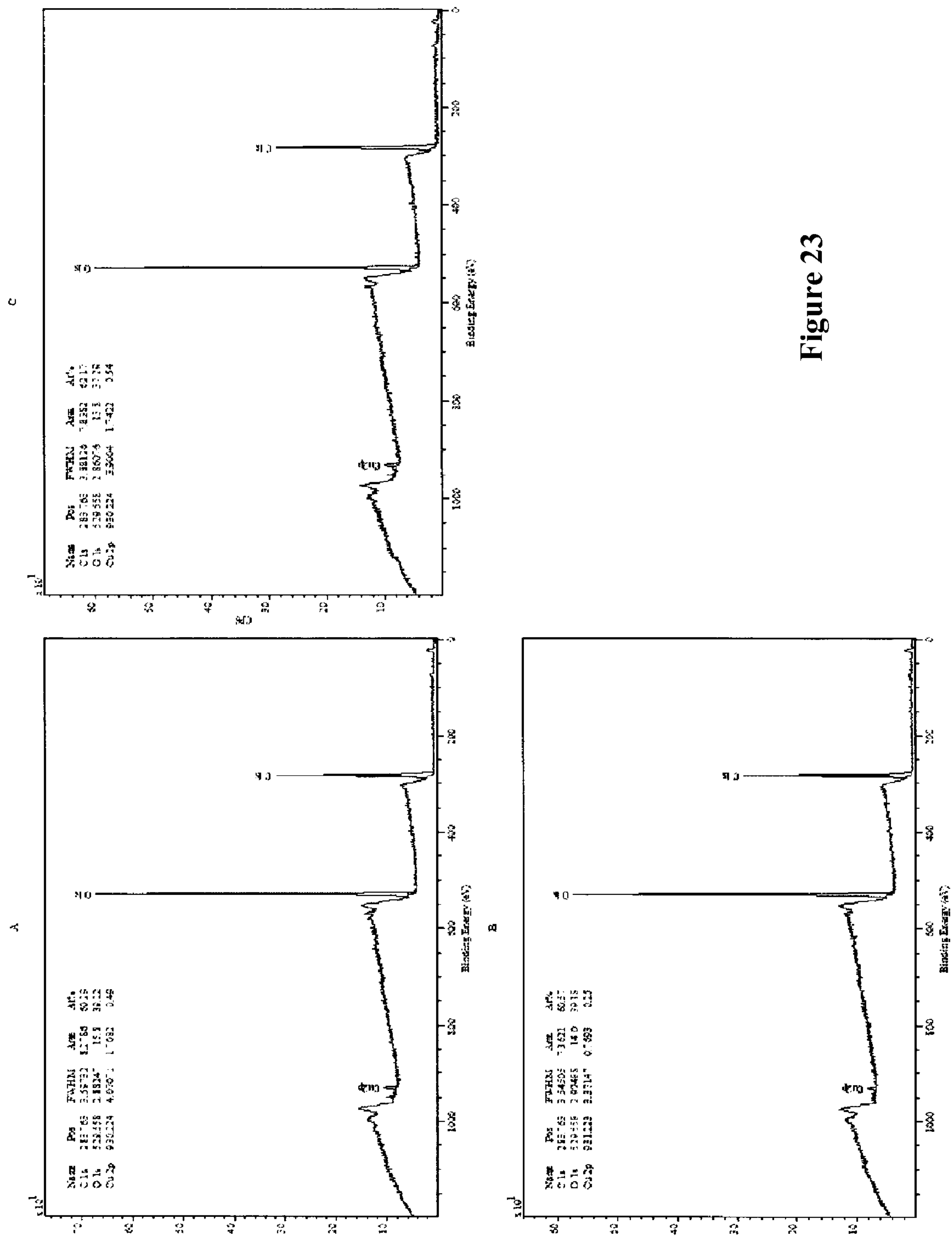
FIG. 23. X-ray photoelectron spectroscopy (XPS) of anionic modified cellulose after in situ synthesis of MOF 199 following different experimental procedures: Experiment A (A), Experiment B (B) and Experiment C (C).

FIG. 23 shows XPS of the anionic-modified cellulose after in situ synthesis of MOF 199 following experimental procedures A, B and C. It shows the difference on chemical composition of cellulose derivatives due to the surface modification and provides confirmation of copper presence in the anionic-modified cellulose after in situ synthesis. The results of the XPS are tabulated above.

Figure 24:
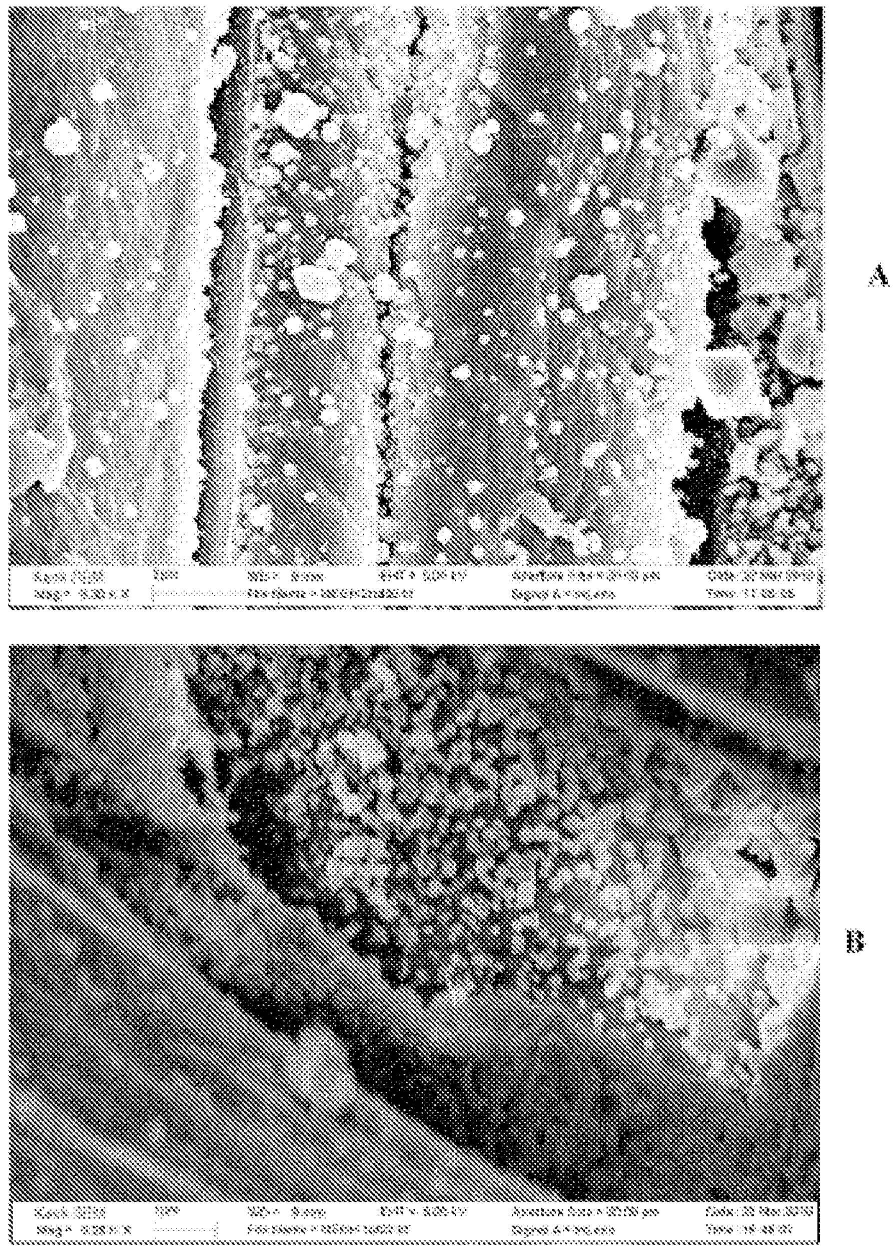
FIG. 24. Field Emisson Scanning Electron Microscopy (FESEM) images of anionic modified cellulose after in situ synthesis of MOF 199 following the experiment A (A) and experiment C (B).

FIG. 24 shows the FESEM images from experiments A and C. The surface morphology of the anionic-modified cellulose after in situ synthesis of MOF 199 following the different experimental procedures was compared by using FESEM. From the images, it was possible to observe that in the case of experiment A the crystals were predominantly on the surface of the anionic cellulose. However, in the case of experiment C, the crystals were mostly underneath the anionic cellulose. In addition, Energy Dispersive X-ray Spectroscopy (EDS) was performed to confirm the presence of copper on the crystals.

Figure 25:
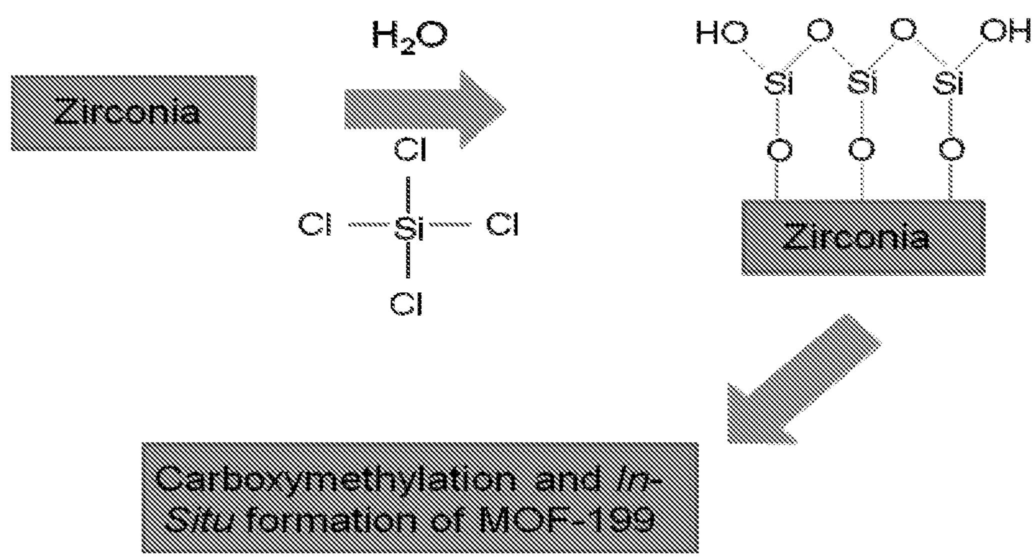
FIG. 25. Schematic for preparation of an example of modified zirconia fibers.

FIG. 25 shows an example of a schematic for the preparation of modified zirconia fibers. First zirconia fibers are modified with water and tetrachlorosilane to obtain the silylated zirconia fibers which are then carboxymethylated allowing for in-situ MOF formation.

Figure 26:
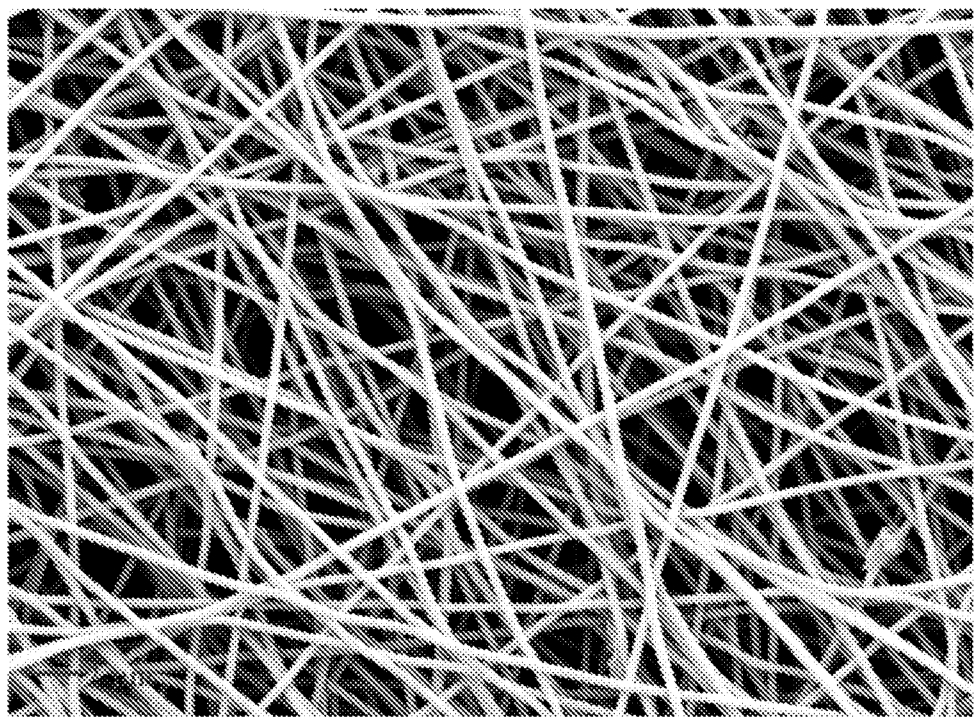
FIG. 26. SEM micrograph of zirconium oxide (2 μm).
Figure 27:
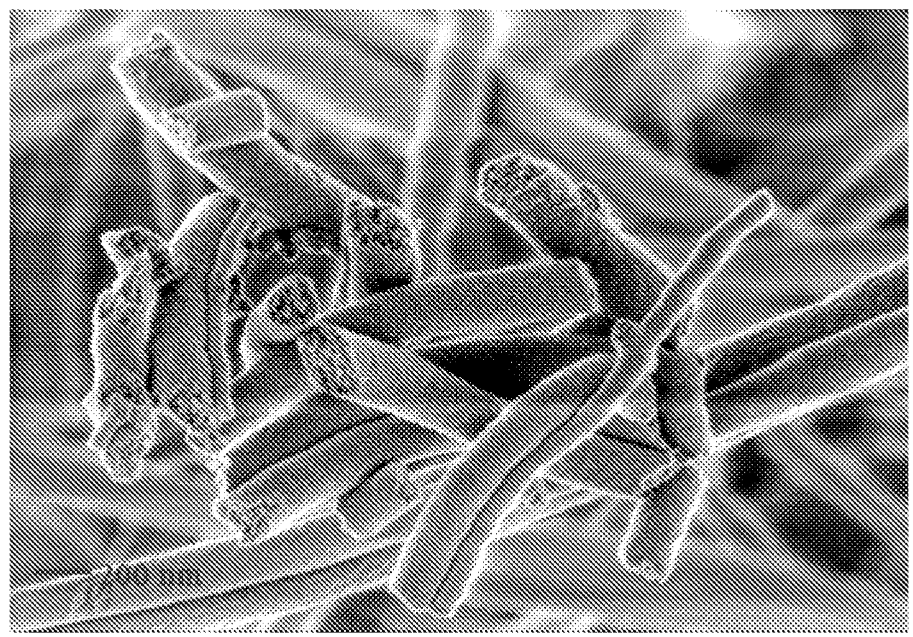
FIG. 27. SEM micrograph of zirconium oxide (200 nm).
Figure 28:
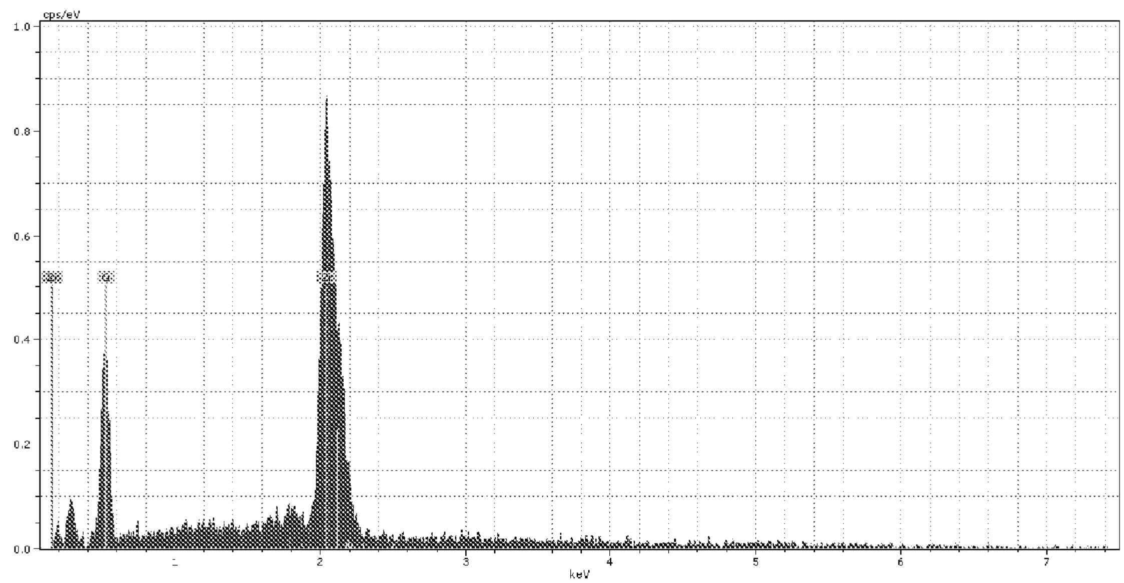
FIG. 28. An example of an EDS (Energy Dispersive X-ray Spectroscopy) spectrum of zirconium oxide nanofibers indicating successful formation pure zirconium oxide.

FIG. 26 shows an SEM image of zirconium oxide (2 μm) whereas FIG. 27 shows an enlarged SEM image of zirconium oxide (200 μm). FIG. 28 shows an EDS spectra of zirconium oxide.

Figure 29:
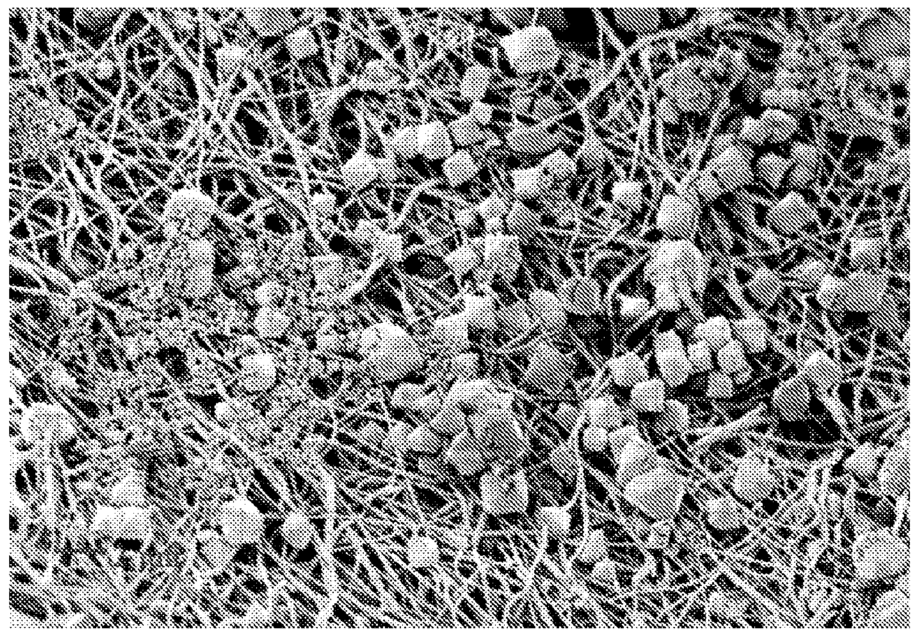
FIG. 29. SEM images of an example of modified zirconia fibers after attachment of MOF 199 (2 μm).
Figure 30:
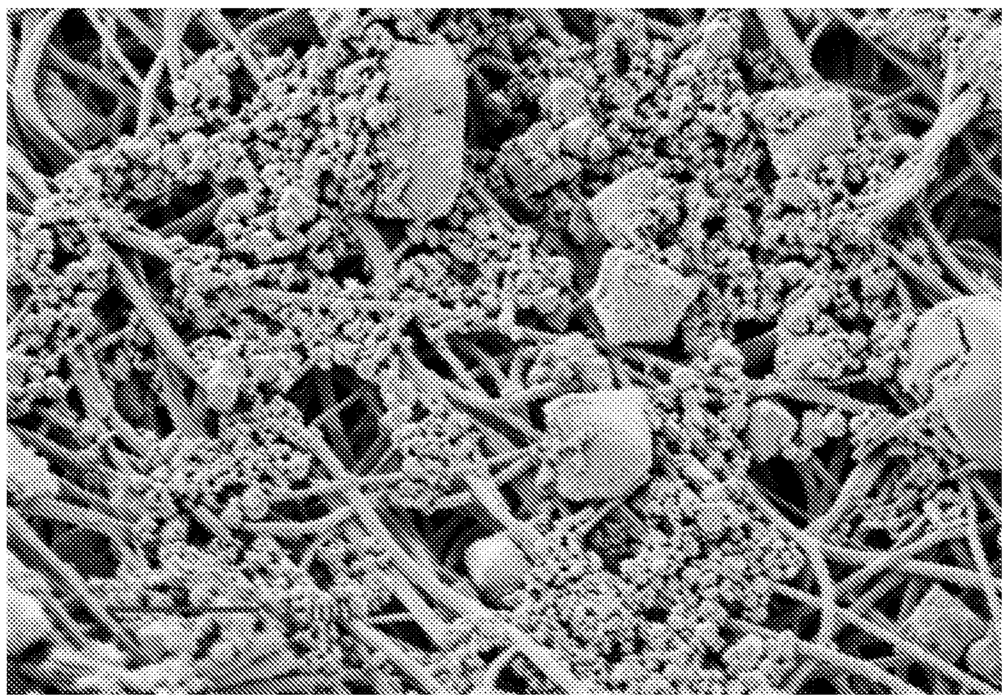
FIG. 30. Magnified SEM images of an example of modified zirconia fibers after attachment of MOF 199 (2 μm).
Figure 31:
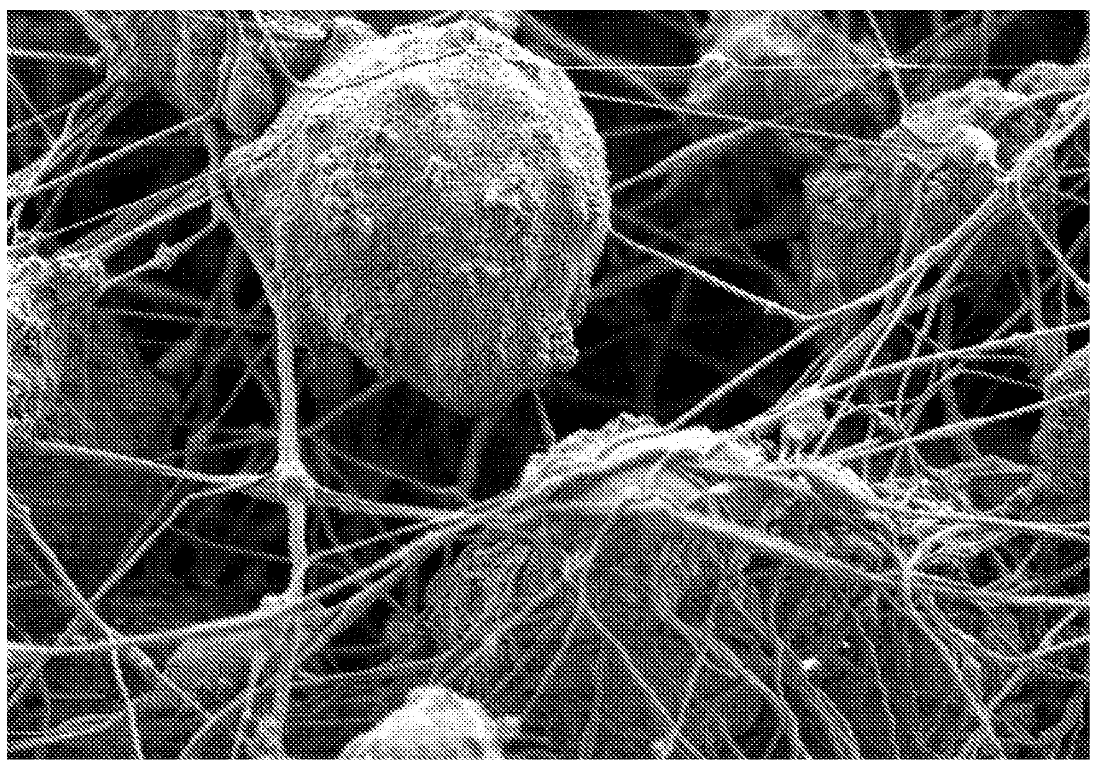
FIG. 31. A SEM of an example of polyacrylonitrile fibers modified with MOF 199 as described in Example 10.
Figure 32:
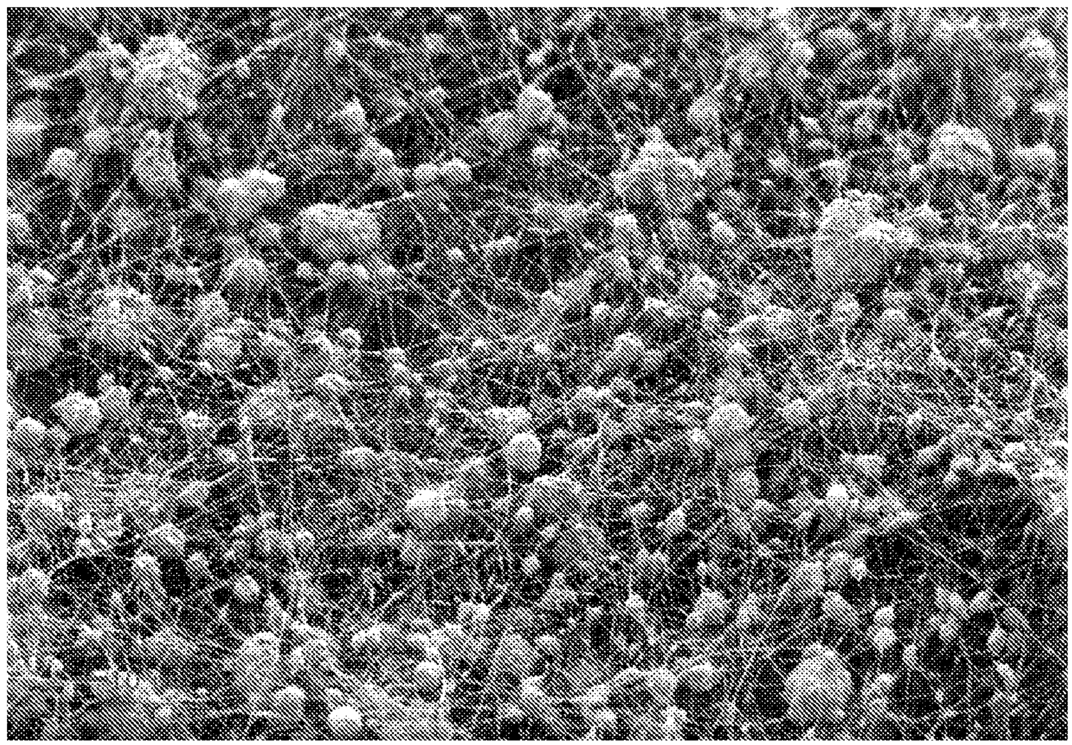
FIG. 32. A SEM of an example of polyacrylonitrile fibers modified with MOF 199 as described in Example 10.
Figure 33:
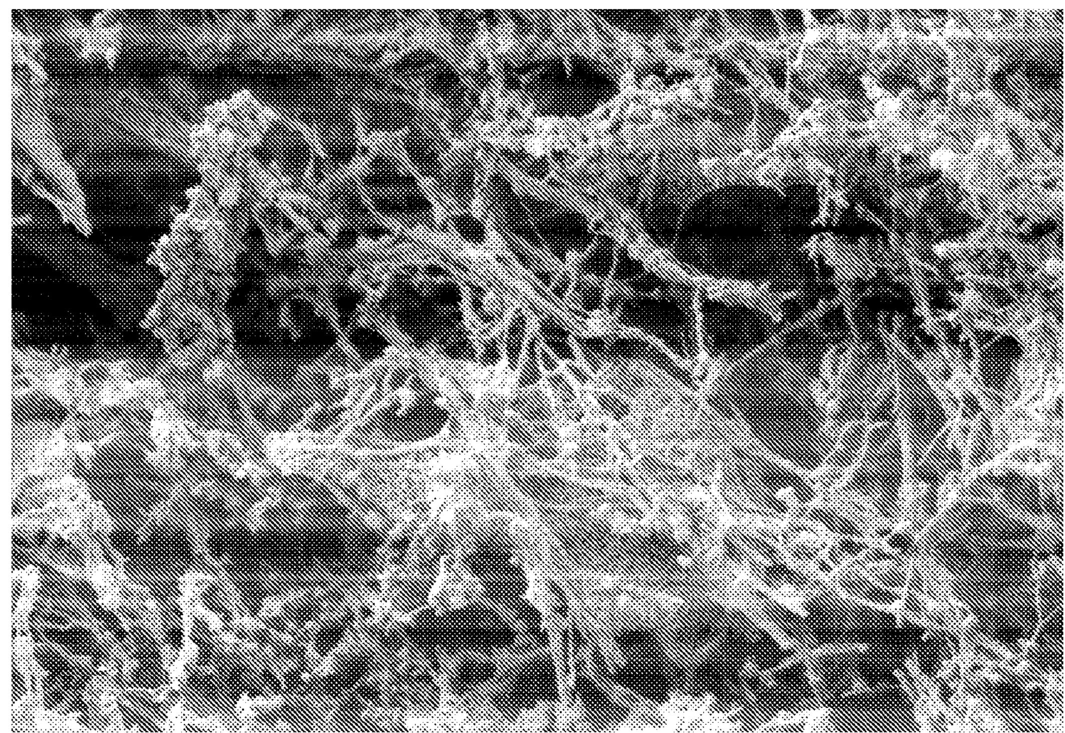
FIG. 33. A SEM of an example of polyacrylonitrile fibers modified with MOF 199 as described in Example 10.

FIG. 29 shows SEM images of an example of modified zirconia fibers after attachment of MOF 199 (2 μm). FIG. 30 shows enlarged SEM images of an example of modified zirconia fibers after attachment of MOF 199 (2 μm).

While the invention has been particularly shown and described with reference to specific embodiments (some of which are preferred embodiments), it should be understood by those having skill in the art that various changes in form and detail may be made therein without departing from the spirit and scope of the present invention as disclosed herein.

The invention claimed is:

1. A material having at least one dimension from 10 nm to 1000 μm and at least one metal-organic framework (MOF) covalently bound to the material, wherein the material is an organic fiber or an inorganic fiber.

2. The material of claim 1, wherein the MOF is covalently bound to the material through a functional group selected from alkyl, ester, acetate, alcohol, amine, amide, carboxylate, and thiol.

3. The material of claim 1, wherein the organic fiber is a cellulose fiber, polyacrylonitrile (PAN) fiber, or a Nylon™ fiber.

4. The material of claim 1, wherein the inorganic fiber is a zirconia fiber.

5. The material of claim 1, wherein the MOF is MOF 199, MOF 76, or a mixture thereof.

6. The material of claim 1, wherein the fiber has from 0.1 to 45% by weight of MOFs.

7. The material of claim 1, wherein the fiber has at least 1% surface coverage of MOFs.

8. A method for selectively absorbing a gas or liquid comprising exposing the material of claim 1 to a mixture comprising at least one gas or liquid, wherein the material selectively absorbs the at least one gas or liquid.

9. The method of claim 8, wherein the gas is hydrogen, methane, ammonia, carbon monoxide, or carbon dioxide.

10. A method of making MOF-modified materials, comprising the steps of:

a) providing a material having at least one dimension from 10 nm to 1000 μm, wherein the material is an organic fiber or an inorganic fiber; and b) exposing the material to a mixture of MOF precursors, under conditions resulting in the formation of at least one MOF that is covalently bound to the material.

11. The method of claim 10, wherein the fibers are modified cellulose fibers selected from ester-modified cellulose fibers or anionic-modified cellulose fibers.

12. The method of claim 11, wherein the MOF-modified material is formed by exposing the modified cellulose fibers to a mixture comprising 1,3,5-benzenetricarboxylic acid, copper (II) acetate, and triethylamine.

* * * * *